(12) United States Patent
Beira

(10) Patent No.: US 11,571,195 B2
(45) Date of Patent: Feb. 7, 2023

(54) STERILE INTERFACE FOR ARTICULATED SURGICAL INSTRUMENTS

(71) Applicant: Distalmotion SA, Epalinges (CH)

(72) Inventor: Ricardo Daniel Rita Beira, Lausanne (CH)

(73) Assignee: Distalmotion SA, Epalinges (CH)

( * ) Notice: Subject to any disclaimer, the term of this patent is extended or adjusted under 35 U.S.C. 154(b) by 56 days.

(21) Appl. No.: 17/351,118

(22) Filed: Jun. 17, 2021

(65) Prior Publication Data

US 2021/0307737 A1  Oct. 7, 2021

Related U.S. Application Data

(62) Division of application No. 15/536,573, filed as application No. PCT/IB2015/002487 on Dec. 18, 2015, now Pat. No. 11,039,820.

(Continued)

(51) Int. Cl.
*A61B 46/10* (2016.01)
*A61B 17/00* (2006.01)
(Continued)

(52) U.S. Cl.
CPC ........ *A61B 17/00234* (2013.01); *A61B 34/30* (2016.02); *A61B 34/35* (2016.02);
(Continued)

(58) Field of Classification Search
CPC ......... A61B 34/10; A61B 34/30; A61B 34/35; A61B 34/70; A61B 46/10; A61B 1/00142;
(Continued)

(56) References Cited

U.S. PATENT DOCUMENTS 2,764,301 A   9/1956  Goertz et al.
2,771,199 A   11/1956 Jelatis
(Continued)

FOREIGN PATENT DOCUMENTS

CN   101027010 A   8/2007
CN   101584594 A   11/2009
(Continued)

OTHER PUBLICATIONS

US 9,232,978 B2, 01/2016, Shellenberger et al. (withdrawn)
(Continued)

*Primary Examiner* — Camtu T Nguyen
(74) *Attorney, Agent, or Firm* — Eversheds Sutherland (US) LLP; Christopher C. Bolten; Albert K. Heng

(57) ABSTRACT

A sterile interface for a surgical platform is provided, optionally to be used with a mechanical telemanipulator. The sterile interface is configured to allow for transmission of motion without dimensional inconsistencies between a non-sterile surgical platform and a sterile surgical instrument that are related to one another in a master-slave configuration. The sterile interface is configured to allow for multiple changes of sterile surgical instruments during a surgical procedure without contaminating the sterile field. The sterile interface allows for interchangeable sterile articulated surgical instruments to be attached to the surgical platform without coming into contact with non-sterile portions of the surgical platform.

20 Claims, 23 Drawing Sheets

Related U.S. Application Data

(60) Provisional application No. 62/094,079, filed on Dec. 19, 2014.

(51) Int. Cl.
    *A61B 34/00*     (2016.01)
    *A61B 34/30*     (2016.01)
    *A61B 34/35*     (2016.01)
    *B25J 19/00*     (2006.01)
    *A61B 90/00*     (2016.01)

(52) U.S. Cl.
    CPC .............. *A61B 34/70* (2016.02); *A61B 46/10* (2016.02); *B25J 19/0075* (2013.01); *A61B 2017/00477* (2013.01); *A61B 2034/302* (2016.02); *A61B 2090/0813* (2016.02)

(58) Field of Classification Search
    CPC .... A61B 17/00234; A61B 2017/00477; A61B 2017/00464; A61B 2017/00367; B23Q 11/08; Y10S 901/49
    See application file for complete search history.

(56) References Cited

U.S. PATENT DOCUMENTS

| | | | |
|---|---|---|---|
| 2,774,488 A | 12/1956 | Goertz et al. | |
| 2,846,084 A | 8/1958 | Goertz et al. | |
| 3,065,863 A | 11/1962 | Saunders, Jr. et al. | |
| 3,095,096 A | 6/1963 | Chesley | |
| 3,212,651 A | 10/1965 | Specht et al. | |
| 3,261,480 A | 7/1966 | Haaker et al. | |
| 3,297,172 A | 1/1967 | Haaker et al. | |
| 3,391,801 A | 7/1968 | Haaker | |
| 3,425,569 A | 2/1969 | Haaker et al. | |
| 4,221,516 A | 9/1980 | Haaker et al. | |
| 4,522,196 A * | 6/1985 | Cunningham | A61B 1/042 600/122 |
| 4,756,655 A | 7/1988 | Jameson | |
| 5,147,357 A | 9/1992 | Rose et al. | |
| 5,176,352 A | 1/1993 | Braun | |
| 5,207,114 A | 5/1993 | Salisbury, Jr. et al. | |
| 5,209,747 A | 5/1993 | Knoepfler | |
| 5,304,203 A | 4/1994 | El-Mallawany et al. | |
| 5,308,358 A | 5/1994 | Bond et al. | |
| 5,330,502 A | 7/1994 | Hassler et al. | |
| 5,368,606 A | 11/1994 | Marlow et al. | |
| 5,383,888 A | 1/1995 | Zvenyatsky et al. | |
| 5,484,435 A | 1/1996 | Fleenor et al. | |
| 5,591,119 A * | 1/1997 | Adair | A61B 46/10 600/122 |
| 5,599,151 A | 2/1997 | Daum et al. | |
| 5,603,723 A | 2/1997 | Aranyi et al. | |
| 5,631,973 A | 5/1997 | Green | |
| 5,649,955 A | 7/1997 | Hashimoto et al. | |
| 5,649,956 A | 7/1997 | Jensen et al. | |
| 5,710,870 A | 1/1998 | Ohm et al. | |
| 5,716,352 A | 2/1998 | Viola et al. | |
| 5,735,874 A | 4/1998 | Measamer et al. | |
| 5,779,727 A | 7/1998 | Orejola | |
| 5,784,542 A | 7/1998 | Ohm et al. | |
| 5,792,045 A | 8/1998 | Adair | |
| 5,797,900 A | 8/1998 | Madhani et al. | |
| 5,810,716 A | 9/1998 | Mukherjee et al. | |
| 5,810,805 A | 9/1998 | Sutcu et al. | |
| 5,828,813 A | 10/1998 | Ohm | |
| 5,908,436 A | 6/1999 | Cuschieri et al. | |
| 5,931,832 A | 8/1999 | Jensen | |
| 5,951,587 A | 9/1999 | Qureshi et al. | |
| 5,976,122 A | 11/1999 | Madhani et al. | |
| 6,026,701 A | 2/2000 | Reboulet | |
| 6,063,095 A | 5/2000 | Wang et al. | |
| 6,132,368 A | 10/2000 | Cooper | |
| 6,197,017 B1 | 3/2001 | Brock et al. | |
| 6,206,903 B1 | 3/2001 | Ramans | |
| 6,233,504 B1 | 5/2001 | Das et al. | |
| 6,281,651 B1 | 8/2001 | Haanpaa et al. | |
| 6,312,435 B1 | 11/2001 | Wallace et al. | |
| 6,331,181 B1 | 12/2001 | Tierney et al. | |
| 6,358,249 B1 | 3/2002 | Chen et al. | |
| 6,361,534 B1 | 3/2002 | Chen et al. | |
| 6,364,879 B1 | 4/2002 | Chen et al. | |
| 6,371,952 B1 | 4/2002 | Madhani et al. | |
| 6,375,610 B2 * | 4/2002 | Verschuur | A61B 46/10 600/125 |
| 6,394,998 B1 | 5/2002 | Wallace et al. | |
| 6,435,794 B1 | 8/2002 | Springer | |
| 6,436,107 B1 | 8/2002 | Wang et al. | |
| 6,459,926 B1 | 10/2002 | Nowlin et al. | |
| 6,491,701 B2 | 12/2002 | Tierney et al. | |
| 6,554,844 B2 | 4/2003 | Lee et al. | |
| 6,587,750 B2 | 7/2003 | Gerbi et al. | |
| 6,594,552 B1 | 7/2003 | Nowlin et al. | |
| 6,671,581 B2 | 12/2003 | Niemeyer et al. | |
| 6,699,177 B1 | 3/2004 | Wang et al. | |
| 6,786,896 B1 | 9/2004 | Madhani et al. | |
| 6,788,999 B2 | 9/2004 | Green | |
| 6,799,065 B1 | 9/2004 | Niemeyer | |
| 6,840,938 B1 | 1/2005 | Morley et al. | |
| 6,850,817 B1 | 2/2005 | Green | |
| 6,852,107 B2 | 2/2005 | Wang et al. | |
| 6,879,880 B2 | 4/2005 | Nowlin et al. | |
| 6,902,560 B1 | 6/2005 | Morley et al. | |
| 6,913,613 B2 | 7/2005 | Schwarz et al. | |
| 6,951,535 B2 | 10/2005 | Ghodoussi et al. | |
| 6,991,627 B2 | 1/2006 | Madhani et al. | |
| 6,994,708 B2 | 2/2006 | Manzo | |
| 7,025,064 B2 | 4/2006 | Wang et al. | |
| 7,048,745 B2 | 5/2006 | Tierney et al. | |
| 7,083,571 B2 | 8/2006 | Wang et al. | |
| 7,090,637 B2 | 8/2006 | Danitz et al. | |
| 7,101,363 B2 | 9/2006 | Nishizawa et al. | |
| 7,122,032 B2 * | 10/2006 | Shinmura | A61B 90/36 606/34 |
| 7,204,836 B2 | 4/2007 | Wagner et al. | |
| 7,232,440 B2 | 6/2007 | Dumbauld et al. | |
| 7,241,289 B2 | 7/2007 | Braun | |
| 7,306,597 B2 | 12/2007 | Manzo | |
| 7,316,681 B2 | 1/2008 | Madhani et al. | |
| 7,338,513 B2 | 3/2008 | Lee et al. | |
| 7,364,582 B2 | 4/2008 | Lee | |
| 7,373,219 B2 | 5/2008 | Nowlin et al. | |
| 7,398,707 B2 | 7/2008 | Morley et al. | |
| 7,481,824 B2 | 1/2009 | Boudreaux et al. | |
| 7,549,998 B2 | 6/2009 | Braun | |
| 7,594,912 B2 | 9/2009 | Cooper et al. | |
| 7,608,039 B1 | 10/2009 | Todd | |
| 7,615,002 B2 | 11/2009 | Rothweiler et al. | |
| 7,615,067 B2 | 11/2009 | Lee et al. | |
| 7,674,255 B2 | 3/2010 | Braun | |
| 7,699,855 B2 | 4/2010 | Anderson et al. | |
| 7,756,036 B2 | 7/2010 | Druke et al. | |
| 7,819,894 B2 | 10/2010 | Mitsuishi et al. | |
| 7,824,401 B2 | 11/2010 | Manzo et al. | |
| 7,828,798 B2 | 11/2010 | Buysse et al. | |
| 7,833,156 B2 | 11/2010 | Williams et al. | |
| 7,890,211 B2 | 2/2011 | Green | |
| 7,914,521 B2 | 3/2011 | Wang et al. | |
| 7,976,458 B2 | 7/2011 | Stefanchik et al. | |
| 8,048,084 B2 | 11/2011 | Schneid | |
| 8,105,320 B2 | 1/2012 | Manzo | |
| 8,114,017 B2 | 2/2012 | Bacher | |
| 8,137,263 B2 | 3/2012 | Marescaux et al. | |
| 8,142,447 B2 | 3/2012 | Cooper et al. | |
| 8,224,485 B2 | 7/2012 | Unsworth | |
| 8,246,617 B2 | 8/2012 | Welt et al. | |
| 8,267,958 B2 | 9/2012 | Braun | |
| 8,287,469 B2 | 10/2012 | Stefanchik et al. | |
| 8,292,889 B2 | 10/2012 | Cunningham et al. | |
| 8,306,656 B1 | 11/2012 | Schaible et al. | |
| 8,308,738 B2 | 11/2012 | Nobis et al. | |
| 8,332,072 B1 | 12/2012 | Schaible et al. | |
| 8,336,751 B2 | 12/2012 | Scirica | |
| 8,347,754 B1 | 1/2013 | Veltri et al. | |

(56) References Cited

U.S. PATENT DOCUMENTS

| | | |
|---|---|---|
| 8,353,898 B2 | 1/2013 | Lutze et al. |
| 8,357,161 B2 | 1/2013 | Mueller |
| 8,382,742 B2 | 2/2013 | Hermann et al. |
| 8,388,516 B2 | 3/2013 | Sholev |
| 8,403,832 B2 | 3/2013 | Cunningham et al. |
| 8,414,475 B2 | 4/2013 | Sholev |
| 8,418,904 B2 | 4/2013 | Wenchell et al. |
| 8,423,186 B2 | 4/2013 | Itkowitz et al. |
| 8,433,389 B2 | 4/2013 | Geiger et al. |
| 8,435,171 B2 | 5/2013 | Sholev |
| 8,496,152 B2 | 7/2013 | Viola |
| 8,518,024 B2 | 8/2013 | Williams et al. |
| 8,523,900 B2 | 9/2013 | Jinno et al. |
| 8,540,748 B2 | 9/2013 | Murphy et al. |
| 8,562,592 B2 | 10/2013 | Conlon et al. |
| 8,568,444 B2 | 10/2013 | Cunningham |
| 8,579,176 B2 | 11/2013 | Smith et al. |
| 8,591,397 B2 | 11/2013 | Berkelman et al. |
| 8,597,280 B2 | 12/2013 | Cooper et al. |
| 8,602,287 B2 | 12/2013 | Yates et al. |
| 8,603,077 B2 | 12/2013 | Cooper et al. |
| 8,616,431 B2 | 12/2013 | Timm et al. |
| 8,617,203 B2 | 12/2013 | Stefanchik et al. |
| 8,663,270 B2 | 3/2014 | Donnigan et al. |
| 8,668,689 B2 | 3/2014 | Dumbauld et al. |
| 8,668,702 B2 | 3/2014 | Awtar et al. |
| 8,690,755 B2 | 4/2014 | Sholev |
| 8,696,666 B2 | 4/2014 | Sanai et al. |
| 8,709,000 B2 | 4/2014 | Madhani et al. |
| 8,761,930 B2 | 6/2014 | Nixon |
| 8,768,509 B2 | 7/2014 | Unsworth |
| 8,792,688 B2 | 7/2014 | Unsworth |
| 8,801,752 B2 | 8/2014 | Fortier et al. |
| 8,816,628 B2 | 8/2014 | Nowlin et al. |
| 8,818,560 B2 | 8/2014 | Kishi |
| 8,821,480 B2 | 9/2014 | Burbank |
| 8,827,135 B2 | 9/2014 | Amid et al. |
| 8,828,046 B2 | 9/2014 | Stefanchik et al. |
| 8,845,517 B2 | 9/2014 | Russo |
| 8,845,622 B2 | 9/2014 | Paik et al. |
| 8,870,049 B2 | 10/2014 | Amid et al. |
| 8,870,867 B2 | 10/2014 | Walberg et al. |
| 8,887,979 B2 | 11/2014 | Mastri et al. |
| 8,894,674 B2 | 11/2014 | Balanev et al. |
| 8,919,348 B2 | 12/2014 | Williams et al. |
| 8,930,027 B2 | 1/2015 | Schaible et al. |
| 8,945,098 B2 | 2/2015 | Seibold et al. |
| 8,961,499 B2 | 2/2015 | Paik et al. |
| 8,961,514 B2 | 2/2015 | Garrison |
| 8,968,187 B2 | 3/2015 | Kleyman et al. |
| 8,989,844 B2 | 3/2015 | Cinquin et al. |
| 8,992,564 B2 | 3/2015 | Jaspers |
| 9,023,015 B2 | 5/2015 | Penna |
| 9,033,998 B1 | 5/2015 | Schaible et al. |
| 9,044,238 B2 | 6/2015 | Orszulak |
| 9,084,606 B2 | 7/2015 | Greep |
| 9,113,860 B2 | 8/2015 | Viola et al. |
| 9,113,861 B2 | 8/2015 | Martin et al. |
| 9,149,339 B2 | 10/2015 | Unsworth |
| 9,204,939 B2 | 12/2015 | Frimer et al. |
| 9,216,013 B2 | 12/2015 | Scirica et al. |
| 9,295,379 B2 | 3/2016 | Sholev |
| 9,307,894 B2 | 4/2016 | Von Grunberg et al. |
| 9,333,040 B2 | 5/2016 | Shellenberger et al. |
| 9,345,545 B2 | 5/2016 | Shellenberger et al. |
| 9,360,934 B2 | 6/2016 | Ruiz Morales et al. |
| 9,421,003 B2 | 8/2016 | Williams et al. |
| 9,474,580 B2 | 10/2016 | Hannaford et al. |
| 9,480,531 B2 | 11/2016 | Von Grunberg |
| 9,492,240 B2 | 11/2016 | Itkowitz et al. |
| 9,504,456 B2 | 11/2016 | Frimer et al. |
| 9,603,672 B2 | 3/2017 | Shellenberger et al. |
| 9,669,542 B2 | 6/2017 | Karguth et al. |
| 9,696,700 B2 | 7/2017 | Beira et al. |
| 9,757,204 B2 | 9/2017 | Frimer et al. |
| 9,757,206 B2 | 9/2017 | Frimer et al. |
| 9,763,741 B2 | 9/2017 | Alvarez et al. |
| 9,795,282 B2 | 10/2017 | Sholev et al. |
| 9,795,454 B2 | 10/2017 | Seeber et al. |
| 9,877,794 B2 | 1/2018 | Csiky |
| D816,243 S | 4/2018 | Barber |
| 9,937,013 B2 | 4/2018 | Frimer et al. |
| 9,943,372 B2 | 4/2018 | Sholev et al. |
| 10,028,792 B2 | 7/2018 | Frimer et al. |
| 10,039,609 B2 | 8/2018 | Frimer et al. |
| 10,039,820 B2 * | 8/2018 | Coller .................... A61P 31/14 |
| 10,052,157 B2 | 8/2018 | Frimer et al. |
| 10,064,691 B2 | 9/2018 | Frimer et al. |
| 10,071,488 B2 | 9/2018 | Robinson et al. |
| 10,092,164 B2 | 10/2018 | Sholev et al. |
| 10,092,359 B2 | 10/2018 | Beira et al. |
| 10,092,365 B2 | 10/2018 | Seeber |
| 10,136,956 B2 | 11/2018 | Seeber |
| 10,201,392 B2 | 2/2019 | Frimer et al. |
| 10,265,129 B2 | 4/2019 | Beira |
| 10,325,072 B2 | 6/2019 | Beira et al. |
| 10,357,320 B2 | 7/2019 | Beira |
| 10,357,324 B2 * | 7/2019 | Flatt ...................... A61B 90/50 |
| 10,363,055 B2 | 7/2019 | Beira et al. |
| 10,413,374 B2 | 9/2019 | Chassot et al. |
| 10,510,447 B2 | 12/2019 | Beira et al. |
| 10,548,680 B2 | 2/2020 | Beira |
| 10,568,709 B2 | 2/2020 | Beira |
| 10,646,294 B2 | 5/2020 | Beira |
| 10,786,272 B2 | 9/2020 | Beira |
| 2002/0040217 A1 | 4/2002 | Jinno |
| 2002/0049367 A1 | 4/2002 | Irion et al. |
| 2002/0072736 A1 | 6/2002 | Tierney et al. |
| 2002/0082612 A1 | 6/2002 | Moll et al. |
| 2003/0013949 A1 | 1/2003 | Moll et al. |
| 2003/0155747 A1 | 8/2003 | Bridges |
| 2003/0208186 A1 | 11/2003 | Moreyra |
| 2004/0049205 A1 | 3/2004 | Lee et al. |
| 2004/0116906 A1 | 6/2004 | Lipow |
| 2004/0236316 A1 | 11/2004 | Danitz et al. |
| 2004/0253079 A1 | 12/2004 | Sanchez |
| 2005/0096502 A1 | 5/2005 | Khalili |
| 2005/0204851 A1 | 9/2005 | Morley et al. |
| 2005/0240078 A1 | 10/2005 | Kwon et al. |
| 2006/0043698 A1 | 3/2006 | Bridges |
| 2006/0079884 A1 | 4/2006 | Manzo et al. |
| 2006/0178559 A1 | 8/2006 | Kumar et al. |
| 2006/0183975 A1 | 8/2006 | Saadat et al. |
| 2006/0219065 A1 | 10/2006 | Jinno et al. |
| 2006/0235436 A1 | 10/2006 | Anderson et al. |
| 2006/0253109 A1 | 11/2006 | Chu |
| 2007/0088340 A1 | 4/2007 | Brock et al. |
| 2007/0137371 A1 | 6/2007 | Devengenzo et al. |
| 2007/0156123 A1 | 7/2007 | Moll et al. |
| 2007/0208375 A1 | 9/2007 | Nishizawa et al. |
| 2007/0299387 A1 | 12/2007 | Williams et al. |
| 2008/0039255 A1 | 2/2008 | Jinno et al. |
| 2008/0046122 A1 | 2/2008 | Manzo et al. |
| 2008/0058776 A1 | 3/2008 | Jo et al. |
| 2008/0071208 A1 | 3/2008 | Voegele et al. |
| 2008/0103492 A1 | 5/2008 | Morley et al. |
| 2008/0177285 A1 | 7/2008 | Brock et al. |
| 2008/0243106 A1 | 10/2008 | Coe et al. |
| 2008/0287926 A1 | 11/2008 | Abou El Kheir |
| 2008/0314181 A1 | 12/2008 | Schena |
| 2009/0030449 A1 | 1/2009 | Kawai et al. |
| 2009/0036902 A1 | 2/2009 | DiMaio et al. |
| 2009/0192522 A1 | 7/2009 | Blumenkranz |
| 2009/0198253 A1 | 8/2009 | Omori |
| 2009/0216248 A1 | 8/2009 | Uenohara et al. |
| 2009/0216249 A1 | 8/2009 | Jinno et al. |
| 2009/0247821 A1 | 10/2009 | Rogers |
| 2009/0248039 A1 | 10/2009 | Cooper et al. |
| 2009/0275994 A1 | 11/2009 | Phan et al. |
| 2009/0299141 A1 | 12/2009 | Downey et al. |
| 2009/0326552 A1 | 12/2009 | Diolaiti |
| 2010/0004508 A1 | 1/2010 | Naito et al. |
| 2010/0011900 A1 | 1/2010 | Burbank |
| 2010/0023025 A1 | 1/2010 | Zeiner et al. |

(56) References Cited

U.S. PATENT DOCUMENTS

| | | |
|---|---|---|
| 2010/0082041 A1 | 4/2010 | Prisco |
| 2010/0094130 A1 | 4/2010 | Ninomiya et al. |
| 2010/0121347 A1 | 5/2010 | Jaspers |
| 2010/0160929 A1 | 6/2010 | Rogers et al. |
| 2010/0160940 A1 | 6/2010 | Lutze et al. |
| 2010/0170519 A1 | 7/2010 | Romo et al. |
| 2010/0225209 A1 | 9/2010 | Goldberg et al. |
| 2010/0234857 A1 | 9/2010 | Itkowitz et al. |
| 2010/0286712 A1 | 11/2010 | Won et al. |
| 2010/0305595 A1 | 12/2010 | Hermann |
| 2010/0318099 A1 | 12/2010 | Itkowitz et al. |
| 2010/0318101 A1 | 12/2010 | Choi |
| 2010/0324551 A1 | 12/2010 | Gerhardt |
| 2010/0331859 A1 | 12/2010 | Omori |
| 2011/0087236 A1 | 4/2011 | Stokes et al. |
| 2011/0087238 A1 | 4/2011 | Wang et al. |
| 2011/0213346 A1 | 9/2011 | Morley et al. |
| 2011/0230867 A1 | 9/2011 | Hirschfeld et al. |
| 2011/0275901 A1 | 11/2011 | Shelton, IV |
| 2011/0276084 A1 | 11/2011 | Shelton, IV |
| 2011/0290854 A1 | 12/2011 | Timm et al. |
| 2011/0301419 A1 | 12/2011 | Craft et al. |
| 2012/0010628 A1 | 1/2012 | Cooper et al. |
| 2012/0027762 A1 | 2/2012 | Schofield |
| 2012/0031114 A1 | 2/2012 | Mueller et al. |
| 2012/0049623 A1 | 3/2012 | Nakayama |
| 2012/0095298 A1 | 4/2012 | Stefanchik et al. |
| 2012/0116163 A1 | 5/2012 | Lutze et al. |
| 2012/0132018 A1 | 5/2012 | Tang et al. |
| 2012/0143173 A1 | 6/2012 | Steege et al. |
| 2012/0158014 A1 | 6/2012 | Stefanchik et al. |
| 2012/0191245 A1 | 7/2012 | Fudaba et al. |
| 2012/0209292 A1 | 8/2012 | Devengenzo et al. |
| 2012/0232339 A1 | 9/2012 | Csiky |
| 2012/0253326 A1 | 10/2012 | Kleyman |
| 2012/0277762 A1 | 11/2012 | Lathrop et al. |
| 2012/0283745 A1 | 11/2012 | Goldberg et al. |
| 2012/0289973 A1 | 11/2012 | Prisco et al. |
| 2012/0289974 A1 | 11/2012 | Rogers et al. |
| 2012/0296341 A1 | 11/2012 | Seibold et al. |
| 2013/0123805 A1 | 5/2013 | Park et al. |
| 2013/0144274 A1 | 6/2013 | Stefanchik et al. |
| 2013/0172713 A1 | 7/2013 | Kirschenman |
| 2013/0172906 A1 | 7/2013 | Olson et al. |
| 2013/0245643 A1 | 9/2013 | Woodard, Jr. et al. |
| 2013/0245647 A1 | 9/2013 | Martin et al. |
| 2013/0282027 A1 | 10/2013 | Woodard, Jr. et al. |
| 2013/0303408 A1 | 11/2013 | Indermuhle |
| 2013/0304083 A1 | 11/2013 | Kaercher et al. |
| 2013/0304084 A1 | 11/2013 | Beira et al. |
| 2014/0005681 A1 | 1/2014 | Gee et al. |
| 2014/0018447 A1 | 1/2014 | McGovern et al. |
| 2014/0018780 A1 | 1/2014 | Hirscheld |
| 2014/0018960 A1 | 1/2014 | Itkowitz |
| 2014/0052152 A1 | 2/2014 | Au et al. |
| 2014/0076088 A1 | 3/2014 | Berkelman et al. |
| 2014/0114481 A1 | 4/2014 | Ogawa et al. |
| 2014/0135794 A1 | 5/2014 | Cau |
| 2014/0142595 A1 | 5/2014 | Awtar et al. |
| 2014/0166023 A1 | 6/2014 | Kishi |
| 2014/0180308 A1 | 6/2014 | Von Grunberg |
| 2014/0188091 A1 | 7/2014 | Vidal et al. |
| 2014/0188159 A1 | 7/2014 | Steege |
| 2014/0195010 A1 | 7/2014 | Beira et al. |
| 2014/0200561 A1 | 7/2014 | Ingmanson et al. |
| 2014/0207150 A1 | 7/2014 | Rosa et al. |
| 2014/0229007 A1 | 8/2014 | Kishi |
| 2014/0230595 A1 | 8/2014 | Butt et al. |
| 2014/0249546 A1 | 9/2014 | Shvartsberg et al. |
| 2014/0263541 A1 | 9/2014 | Leimbach et al. |
| 2014/0263553 A1 | 9/2014 | Leimbach et al. |
| 2014/0276950 A1 | 9/2014 | Smaby et al. |
| 2014/0276951 A1 | 9/2014 | Hourtash et al. |
| 2014/0276956 A1 | 9/2014 | Crainich et al. |
| 2014/0277017 A1 | 9/2014 | Leimbach et al. |
| 2014/0350570 A1 | 11/2014 | Lee |
| 2015/0057499 A1 | 2/2015 | Erden et al. |
| 2015/0057702 A1 | 2/2015 | Edmondson et al. |
| 2015/0060517 A1 | 3/2015 | Williams |
| 2015/0066018 A1 | 3/2015 | Doll et al. |
| 2015/0105821 A1 | 4/2015 | Ward et al. |
| 2015/0113933 A1 | 4/2015 | Markt |
| 2015/0142018 A1 | 5/2015 | Sniffin et al. |
| 2015/0150575 A1 | 6/2015 | Hartoumbekis et al. |
| 2015/0173840 A1 | 6/2015 | Lohmeier |
| 2015/0230869 A1 | 8/2015 | Shim et al. |
| 2015/0250547 A1 | 9/2015 | Fukushima et al. |
| 2015/0265355 A1 | 9/2015 | Prestel et al. |
| 2016/0022365 A1 | 1/2016 | Jensen et al. |
| 2016/0051274 A1 | 2/2016 | Howell et al. |
| 2016/0151115 A1 | 6/2016 | Karguth et al. |
| 2016/0220314 A1 | 8/2016 | Huelman et al. |
| 2016/0302876 A1 | 10/2016 | Teichtmann |
| 2016/0346053 A1 | 12/2016 | Beira |
| 2016/0374766 A1 | 12/2016 | Schuh |
| 2017/0020615 A1 | 1/2017 | Koenig et al. |
| 2017/0245954 A1 | 8/2017 | Beira |
| 2017/0252096 A1 | 9/2017 | Felder et al. |
| 2017/0265951 A1 | 9/2017 | Grover et al. |
| 2017/0273749 A1 | 9/2017 | Grover et al. |
| 2017/0308667 A1 | 10/2017 | Beira et al. |
| 2017/0360522 A1 | 12/2017 | Beira |
| 2017/0367778 A1 | 12/2017 | Beira |
| 2018/0000544 A1 | 1/2018 | Beira |
| 2018/0000550 A1 | 1/2018 | Beira |
| 2018/0008358 A1 | 1/2018 | Kostrzewski et al. |
| 2018/0028269 A1 | 2/2018 | Morel et al. |
| 2018/0055583 A1 | 3/2018 | Schuh et al. |
| 2018/0078439 A1 | 3/2018 | Cagle et al. |
| 2018/0110576 A1 | 4/2018 | Kopp |
| 2018/0125519 A1 | 5/2018 | Beira et al. |
| 2018/0125592 A1 | 5/2018 | Beira |
| 2018/0242991 A1 | 8/2018 | Beira |
| 2018/0353252 A1 | 12/2018 | Chassot et al. |
| 2018/0360548 A1 | 12/2018 | Marshall et al. |
| 2019/0133698 A1 | 5/2019 | Beira et al. |
| 2019/0239968 A1 | 8/2019 | Beira |
| 2019/0328473 A1 | 10/2019 | Chassot et al. |
| 2020/0105412 A1 | 4/2020 | Beira |

FOREIGN PATENT DOCUMENTS

| | | |
|---|---|---|
| CN | 101637402 A | 2/2010 |
| CN | 101732093 A | 6/2010 |
| CN | 103717355 A | 4/2014 |
| DE | 4303311 A1 | 8/1994 |
| DE | 19652792 C2 | 5/1999 |
| DE | 10314827 B3 | 4/2004 |
| DE | 10314828 B3 | 7/2004 |
| DE | 102012222755 A1 | 6/2014 |
| DE | 102014205036 A1 | 9/2015 |
| DE | 102014205159 A1 | 9/2015 |
| EP | 0595291 A1 | 5/1994 |
| EP | 0621009 A1 | 10/1994 |
| EP | 0677275 A2 | 10/1995 |
| EP | 0776739 A2 | 6/1997 |
| EP | 1254642 A1 | 11/2002 |
| EP | 1279371 B1 | 12/2004 |
| EP | 1886630 A2 | 2/2008 |
| EP | 1889579 A2 | 2/2008 |
| EP | 1889583 A1 | 2/2008 |
| EP | 2058090 A2 | 5/2009 |
| EP | 1977677 B1 | 8/2009 |
| EP | 2095778 A1 | 9/2009 |
| EP | 1889583 B1 | 4/2011 |
| EP | 2377477 B1 | 5/2012 |
| EP | 2473119 A2 | 7/2012 |
| EP | 2305144 B1 | 10/2012 |
| EP | 2044893 B1 | 7/2013 |
| EP | 2653110 A1 | 10/2013 |
| EP | 2679192 A2 | 1/2014 |
| EP | 2736680 A2 | 6/2014 |
| EP | 2777561 A1 | 9/2014 |
| EP | 2783643 A1 | 10/2014 |

(56) References Cited

FOREIGN PATENT DOCUMENTS

| | | |
|---|---|---|
| EP | 2837340 A1 | 2/2015 |
| EP | 2837354 A1 | 2/2015 |
| EP | 2554131 B1 | 8/2015 |
| EP | 2777561 B1 | 10/2015 |
| EP | 2979657 A1 | 2/2016 |
| EP | 2837340 B1 | 10/2016 |
| EP | 2783643 B1 | 1/2019 |
| GB | 834244 A | 5/1960 |
| GB | 969899 A | 9/1964 |
| JP | 2004041580 A | 2/2004 |
| JP | 2007290096 A | 11/2007 |
| JP | 2008104620 A | 5/2008 |
| JP | 2009018027 A | 1/2009 |
| KR | 20110032444 A | 3/2011 |
| KR | 20130031403 A | 3/2013 |
| SU | 722754 A1 | 3/1980 |
| WO | WO-8200611 A1 | 3/1982 |
| WO | WO-9743942 A1 | 11/1997 |
| WO | WO-9825666 A1 | 6/1998 |
| WO | WO-03067341 A2 | 8/2003 |
| WO | WO-03086219 A2 | 10/2003 |
| WO | WO-2004052171 A2 | 6/2004 |
| WO | WO-2005009482 A2 | 2/2005 |
| WO | WO-2005046500 A1 | 5/2005 |
| WO | WO-2006086663 A2 | 8/2006 |
| WO | WO-2007133065 A1 | 11/2007 |
| WO | WO-2008130235 A2 | 10/2008 |
| WO | WO-2009091497 A2 | 7/2009 |
| WO | WO-2009095893 A2 | 8/2009 |
| WO | WO-2009145572 A2 | 12/2009 |
| WO | WO-2009157719 A2 | 12/2009 |
| WO | WO-2010019001 A2 | 2/2010 |
| WO | WO-2010030114 A2 | 3/2010 |
| WO | WO-2010050771 A2 | 5/2010 |
| WO | WO-2010083480 A2 | 7/2010 |
| WO | WO-2010096580 A1 | 8/2010 |
| WO | WO-2010130817 A1 | 11/2010 |
| WO | WO-2011025818 A1 | 3/2011 |
| WO | WO-2011027183 A2 | 3/2011 |
| WO | WO-2011123669 A1 | 10/2011 |
| WO | WO-2012020386 A1 | 2/2012 |
| WO | WO-2012049623 A1 | 4/2012 |
| WO | WO-2013007784 A1 | 1/2013 |
| WO | WO-2013014621 A2 | 1/2013 |
| WO | WO-2014012780 A1 | 1/2014 |
| WO | WO-2014018447 A1 | 1/2014 |
| WO | WO-2014067804 A1 | 5/2014 |
| WO | WO-2014094716 A1 | 6/2014 |
| WO | WO-2014094717 A1 | 6/2014 |
| WO | WO-2014094718 A1 | 6/2014 |
| WO | WO-2014094719 A1 | 6/2014 |
| WO | WO-2014139023 A1 | 9/2014 |
| WO | WO-2014145148 A2 | 9/2014 |
| WO | WO-2014156221 A1 | 10/2014 |
| WO | WO-2014201010 A1 | 12/2014 |
| WO | WO-2014201538 A1 | 12/2014 |
| WO | WO-2015081946 A1 | 6/2015 |
| WO | WO-2015081947 A1 | 6/2015 |
| WO | WO-2015088647 A1 | 6/2015 |
| WO | WO-2015088655 A1 | 6/2015 |
| WO | WO-2015111475 A1 | 7/2015 |
| WO | WO-2015113933 A1 | 8/2015 |
| WO | WO-2015129383 A1 | 9/2015 |
| WO | WO-2015139674 A1 | 9/2015 |
| WO | WO-2015175200 A1 | 11/2015 |
| WO | WO-2016030767 A1 | 3/2016 |
| WO | WO-2016083189 A1 | 6/2016 |
| WO | WO-2016097861 A1 | 6/2016 |
| WO | WO-2016097864 A2 | 6/2016 |
| WO | WO-2016097868 A1 | 6/2016 |
| WO | WO-2016097871 A1 | 6/2016 |
| WO | WO-2016097873 A2 | 6/2016 |
| WO | WO-2016154173 A1 | 9/2016 |
| WO | WO-2016162751 A1 | 10/2016 |
| WO | WO-2016162752 A1 | 10/2016 |
| WO | WO-2016183054 A1 | 11/2016 |
| WO | WO-2016189284 A1 | 12/2016 |
| WO | WO-2016209891 A1 | 12/2016 |
| WO | WO-2017015599 A1 | 1/2017 |
| WO | WO-2017037532 A1 | 3/2017 |
| WO | WO-2017064301 A1 | 4/2017 |
| WO | WO-2017064303 A1 | 4/2017 |
| WO | WO-2017064305 A1 | 4/2017 |
| WO | WO-2017064306 A1 | 4/2017 |
| WO | WO-2017134077 A1 | 8/2017 |
| WO | WO-2017220978 A1 | 12/2017 |
| WO | WO-2018142112 A1 | 8/2018 |
| WO | WO-2018162921 A1 | 9/2018 |
| WO | WO-2019099346 A2 | 5/2019 |
| WO | WO-2020131304 A1 | 6/2020 |
| WO | WO-2020263870 A1 | 12/2020 |

OTHER PUBLICATIONS

U.S. Appl. No. 13/878,924, now U.S. Pat. No. 10,092,359, filed May 17, 2013, Oct. 9, 2018.
U.S. Appl. No. 14/233,184, now U.S. Pat. No. 9,696,700, filed Jan. 16, 2014, Jul. 4, 2017.
U.S. Appl. No. 15/116,509, now U.S. Pat. No. 10,265,129, filed Aug. 3, 2016, Apr. 23, 2019.
U.S. Appl. No. 15/506,659, now U.S. Pat. No. 10,357,320, filed Feb. 24, 2017, Jul. 23, 2019.
U.S. Appl. No. 15/536,539, now U.S. Pat. No. 10,864,049, filed Jun. 15, 2017, Dec. 15, 2020.
U.S. Appl. No. 15/536,562, now U.S. Pat. No. 10,864,052, filed Jun. 15, 2017, Dec. 15, 2020.
U.S. Appl. No. 15/536,568, now U.S. Pat. No. 10,548,680, filed Jun. 15, 2017, Feb. 4, 2020.
U.S. Appl. No. 15/536,573, now U.S. Pat. No. 11,039,820, filed Jun. 15, 2017, Jun. 22, 2021.
U.S. Appl. No. 15/536,576, now U.S. Pat. No. 10,646,294, filed Jun. 15, 2017, May 12, 2020.
U.S. Appl. No. 15/564,193, now U.S. Pat. No. 10,568,709, filed Oct. 3, 2017, Feb. 25, 2020.
U.S. Appl. No. 15/564,194, now U.S. Pat. No. 10,363,055, filed Oct. 3, 2017, Jul. 30, 2019.
U.S. Appl. No. 15/633,611, now U.S. Pat. No. 10,325,072, filed Jun. 26, 2017, Jun. 18, 2019.
U.S. Appl. No. 15/756,037, now U.S. Pat. No. 10,786,272, filed Feb. 27, 2018, Sep. 29, 2020.
U.S. Appl. No. 15/976,812, filed May 10, 2018.
U.S. Appl. No. 16/153,695, filed Oct. 5, 2018.
U.S. Appl. No. 16/269,383, now U.S. Pat. No. 10,413,374, filed Feb. 6, 2019, Sep. 17, 2019.
U.S. Appl. No. 16/389,854, filed Apr. 19, 2019.
U.S. Appl. No. 16/442,435, now U.S. Pat. No. 10,510,447, filed Jun. 14, 2019, Dec. 17, 2019.
U.S. Appl. No. 16/505,585, filed Jul. 8, 2019.
U.S. Appl. No. 16/701,063, filed Dec. 2, 2019.
U.S. Appl. No. 16/870,870, filed May 8, 2020.
U.S. Appl. No. 17/032,631, filed Sep. 25, 2020.
Abbott, et al., Design of an Endoluminal Notes Robotic System, IEEE/RSJ International Conference on Intelligent Robots and Systems, 2007, San Diego, CA (pp. 410-416).
Aesculap Surgical Technologies, Aesculap.RTM. Caiman™, Advanced Bipolar Seal and Cut Technology Brochure, 6 pages (retrieved Aug. 31, 2015).
Arata, et al., Development of a dexterous minimally-invasive surgical system with augmented force feedback capability, IEEE/RSJ International Conference on Intelligent Robots and Systems, 2005 (pp. 3207-3212).
Cavusoglu, et al., Laparoscopic Telesurgical Workstation, IEEE Transactions on Robotics and Automation, (15)4:728-739 (1999).
Charles, et al., Dexterity-enhanced Telerobotic Microsurgery, 8th International Conference Advanced Robotics, pp. 5-10 (1997).
Communication Relating to the Results of the Partial International Search dated May 28, 2019 in Int'l PCT Patent Appl. Serial No. PCT/IB2019/050961 (1510).

(56) References Cited

OTHER PUBLICATIONS

Dachs, et al., Novel Surgical Robot Design: Minimizing the Operating Envelope With in the Sterile Field, 28th International Conference, IEEE Engineering in Medicine Biology Society, 2006, New York (pp. 1505-1508).
Dario, et al., "Novel Mechatronic Tool for Computer-Assisted Arthroscopy," IEEE Transactions on Information Technology in Biomedicine, 4(1):15-29 (Mar. 2000).
European Search Report dated Dec. 10, 2013 in EP Patent Appl. Serial No. 12767107.1 (0330).
Extended European Search Report dated Mar. 18, 2020 in EP Patent Appl. Serial No. 19213231.4 (1031).
Focacci, et al., Lightweight Hand-held Robot for Laparoscopic Surgery, IEEE International Conference on Robotics & Automation, Rome, Italy, pp. 599-604 (2007).
Guthart, et al., The Intuitive™. Telesurgery System: Overview and Application, IEEE International Conference on Robotics & Automation, San Francisco, CA, 2000 (pp. 618-621).
Ikuta, et al., Development of Remote Microsurgery Robot and New Surgical Procedure for Deep and Narrow Space, IEEE International Conference on Robotics & Automation, Taipei, Taiwan, 2003 (pp. 1103-1108).
Ikuta, et al., Hyper Redundant Miniature Manipulator 'Hyper Finger' for Remote Minimally Invasive Surgery in Deep Area, IEEE International Conference on Robotics & Automation, Taipei, Taiwan, 2003 (pp. 1098-1102).
International Search & Written Opinion dated Jul. 7, 2020 in Int'l PCT Patent Appl. Serial No. PCT/IB2020/050039 (1610).
International Search Report & Written Opinion dated Feb. 2, 2017 in Int'l PCT Patent Appl. Serial No. PCT/IB2016/001286 (1310).
International Search Report & Written Opinion dated Jan. 18, 2013 in Int'l PCT Patent Appl Serial No. PCT/IB2012/053786 (0310).
International Search Report & Written Opinion dated Jul. 10, 2018 in Int'l PCT Patent Appl. Serial No. PCT/IB2018/053272 (1410).
International Search Report & Written Opinion dated Jun. 10, 2016 in Int'l PCT Patent Appl Serial No. PCT/IB2015/002533 (0810).
International Search Report & Written Opinion dated Jun. 13, 2016 in Int'l PCT Patent Appl Serial No. PCT/IB2015/002493 (0710).
International Search Report & Written Opinion dated Mar. 30, 2015 in Int'l PCT Patent Appl Serial No. PCT/EP2015/051473 (0410).
International Search Report & Written Opinion dated May 23, 2016 in Int'l PCT Patent Appl Serial No. PCT/IB2015/002524 (0610).
International Search Report & Written Opinion dated May 24, 2016 in Int'l PCT Patent Appl Serial No. PCT/IB2015/002487 (0910).
International Search Report & Written Opinion dated Sep. 2, 2016 in Int'l PCT Patent Appl Serial No. PCT/IB2016/000543 (1110).
International Search Report & Written Opinion dated Feb. 17, 2016 in Int'l PCT Patent Appl. Serial No. PCT/IB2015/002095 (0510).
International Search Report & Written Opinion dated Mar. 23, 2012 in Int'l PCT Patent Appl. Serial No. PCT/IB2011/054476 (0210).
International Search Report & Written Opinion dated Apr. 26, 2016 in Int'l PCT Patent Appl. Serial No. PCT/IB2015/002512 (1010).
International Search Report & Written Opinion dated Jul. 7, 2020 in Int'l. PCT Patent Appl. Serial No. PCTIB2020050039 (1610).
International Search Report & Written Opinion dated Jul. 23, 2019 in Int'l PCT Patent Appl. No. PCT/IB2019/050961 (1510).
International Search Report & Written Opinion dated Aug. 25, 2016 in Int'l PCT Patent Appl. Serial No. PCT/IB2016/000542 (1210).

Ishii, et al., Development of a New Bending Mechanism and Its Application to Robotic Forceps Manipulator, IEEE International Conference on Robotics & Automation, Rome, Italy, 2007 (pp. 238-243).
Kobayashi, et al., Small Occupancy Robotic Mechanisms for Endoscopic Surgery, International Conference on Medical Image Computing and Computer assisted Interventions, 2002, (pp. 75-82).
Lang, et al., Intra-operative robotics: NeuroArm., Acta Neurochir Suppl, 109:231-236 (2011).
Mayer, et al., The Endo[PA]R System for Minimally Invasive Robotic Surgery, IEEE/RSJ International Conference on Intelligent Robots and Systems, Sendai, Japan, 2004 (pp. 3637-3642).
Mitsuishi, et al., Development of a Remote Minimally Invasive Surgical System with Operational Environment Transmission Capability, IEEE International Conference on Robotics & Automation, Taipei, Taiwan, 2003, (pp. 2663-2670).
Mitsuishi, et al., Master-Slave Robotic Platform and its Feasibility Study for MicroNeurosurgery, Int. J. Med. Robot., 9(2):180-9 (2013).
Morita, et al., Microsurgical Robotic System for the Deep Surgical Field: development of a Prototype and Feasibility Studies in Animal and Cadaveric Models, J. Neurosurg., 103(2):320-7 (2005).
Nakamura, et al., Multi-DOF Forceps Manipulator System for Laparoscopic Surgery-Mechanism miniaturized & Evaluation of New Interface, 4th International Conference on Medical Image Computing and Computer assisted Interventions (MICCAI2001), 2001 (pp. 606-613).
Peirs, et al., "Design of an Advanced Tool Guiding System for Robotic Surgery," IEEE International Conference on Robotics & Automation, Taipei, Taiwan, 2003, (pp. 2651-2656).
Salle, et al., Optimal Design of High Dexterity Modular MIS Instrument for Coronary Artery Bypass Grafting, IEEE International Conference on Robotics & Automation, New Orleans, LA, 2004, (pp. 1276-1281).
Seibold, et al., Prototype of Instrument for Minimally Invasive Surgery with 6-Axis Force Sensing Capability, IEEE International Conference on Robotics & Automation, Barcelona, Spain, 2005, (pp. 496-501).
Simaan, et al., Dexterous System for Laryngeal Surgery: Multi-Backbone Bending Snake-like Slaves for Teleoperated Dexterous Surgical Tool Manipulation, IEEE International Conference on Robotics & Automation, New Orleans, LA, 2004 (pp. 351-357).
Stryker™, Endoscopy, Take a Look Around, Ideal Eyes.TM. FFD122 HD, Articulating Laparoscope Brochure, 2 pages (2009).
Swiss Search Report dated Jun. 4, 2012 in Swiss Patent Application No. CH 00702/12.
Tavakoli, et al., Force Reflective Master-Slave System for Minimally Invasive Surgery, IEEE/RSJ International Conference on Intelligent Robots and Systems, Las Vegas, NV, 2003, (pp. 3077-3082).
Taylor, et al., Steady-Hand Robotic System for Microsurgical Augmentation, The International Journal of Robotics Research, 18(12):1201-1210 (1999).
Www.cttc.co/technologies/maestro-non-robotic-dexterous-laproscopic-instrum-ent-writs-providing-seven-degrees, Maestro: Non-Robotic Dexterous Laproscopic Instrument With a Wrist Providing Seven Degrees of Freedom, accessed Nov. 12, 2015, 4 pages.
Yamashita, et al., Development of Endoscopic Forceps Manipulator Using Multi-Slider Linkage Mechanisms, The 1st Asian Symposium on Computer Aided Surgery-Robotic and Image-Guided Surgery, Ibaraki, Japan, 4 pages (2005).
Zeus, Robotic Surgical System, available at http://allaboutroboticsurgery.com/zeusrobot.html.

* cited by examiner

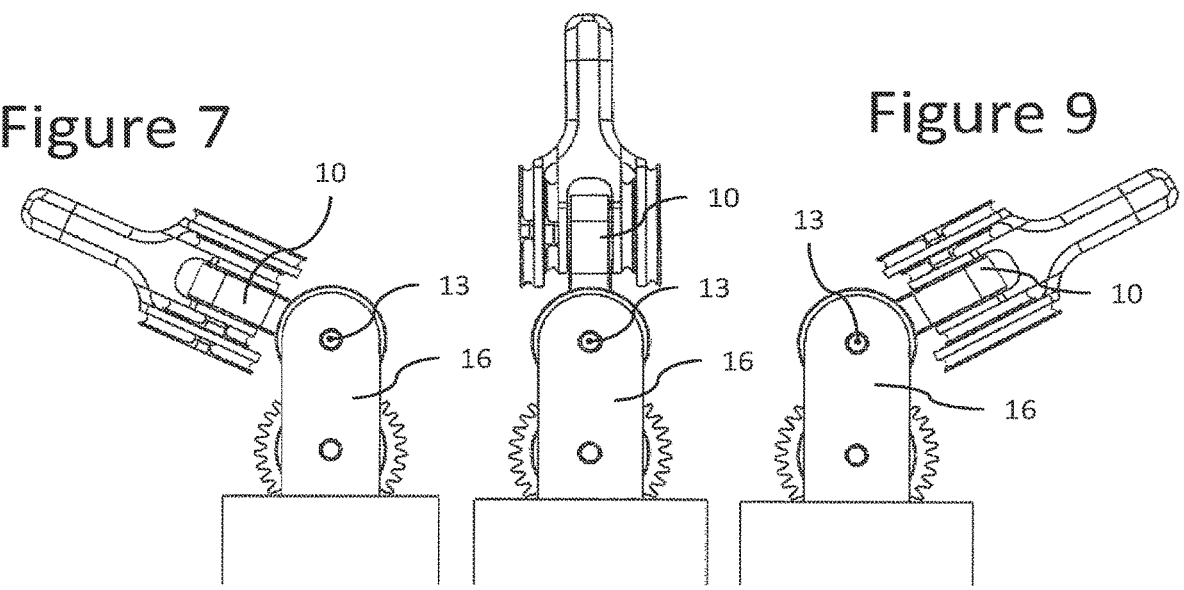

STERILE INTERFACE FOR ARTICULATED SURGICAL INSTRUMENTS

CROSS-REFERENCE TO RELATED APPLICATIONS

This application is a divisional of U.S. patent application Ser. No. 15/536,573, filed Jun. 15, 2017, now U.S. Pat. No. 11,039,820, which is a national phase of International PCT Patent Application Serial No. PCT/IB2015/002487, filed Dec. 18, 2015, which claims the benefit of U.S. Provisional Patent Application Ser. No. 62/094,079, filed Dec. 19, 2014, the entire contents of each of which are incorporated herein by reference.

FIELD OF THE INVENTION

A sterile interface for surgical instruments is provided. More particularly, a sterile interface is provided whereby a sterile instrument portion is attached or detached from a surgical device platform that is not in the sterile field. Even more particularly, the present invention relates to a sterile interface wherein articulated surgical instruments, which may be laparoscopic instruments, may be attached or detached from a surgical platform. The sterile interface allows for the rapid, easy, attachment and detachment of sterile articulated surgical instruments from a surgical platform several times during a surgical procedure, thus allowing the operator to use a multitude of surgical instruments during one procedure while maintaining a sterile surgical field, but while also not requiring the sterilization of the entire surgical platform.

BACKGROUND OF THE INVENTION

Open surgery is still the standard technique for most surgical procedures. It has been used by the medical community for several decades and consists of performing the surgical tasks by a long incision in the abdomen or other body cavity, through which traditional surgical tools are inserted. However, due to the long incision, this approach is extremely invasive for the patient, resulting in substantial blood loos during the surgery and long and painful recovery periods in an in-patient setting.

In order to reduce the invasiveness of open surgery, laparoscopy, a minimally invasive technique, was developed. Instead of a single long incision, one or more smaller incisions are made in the patient through which appropriately sized surgical instruments and endoscopic cameras are inserted. Because of the low degree of invasiveness, laparoscopic techniques reduce blood loss and pain while also shortening hospital stays. When performed by experienced surgeons, these techniques can attain clinical outcomes similar to open surgery. However, despite the above-mentioned advantages, laparoscopy requires advanced surgical skills to manipulate the generally rigid and long instrumentation through small incisions in the patient.

Traditionally, laparoscopic instruments, such as graspers, dissectors, scissors and other tools, have been mounted on straight shafts. These shafts are inserted through small incisions into the patient's body and, because of that, their range of motion inside the body is reduced. The entry incision acts as a point of rotation, decreasing the surgeon's freedom for positioning and orientating the instruments inside the patient. Therefore, due to the drawbacks of currently available instrumentation, laparoscopic procedures are mainly limited to use in simple surgeries, while only a small minority of surgeons is able to use them in complex procedures.

Laparoscopic instruments can be provided as disposable or reusable medical devices. Disposable devices are thrown away after each utilization, without having the need to be cleaned. On the other hand, reusable devices must be cleaned and sterilized after each procedure. In many instances, cost-effectiveness and operating room efficiency requires that instruments be cleaned, sterilized and re-used.

Several laparoscopic instruments may be used during a single surgical procedure. For example, graspers, dissectors and scissors may all need to be used. The present Applicants have demonstrated the use of articulated laparoscopic surgical instruments in conjunction with a mechanical telemanipulator, which allows the surgeon to have control over the instruments with a master-slave configuration based upon mechanical transmission of the surgeon's hand movements to the surgical instruments at pre-determined levels of amplification.

In this context, and in the context of other remotely actuated instrument systems, it is often desirable to detach and attach multiple instruments during a single procedure or period of operation. Particularly in the surgical context, although also when working in delicate, sensitive or contaminated environments, it is often desirable to create a sterile interface wherein the instruments being attached and detached are sterile but the platform to which they are attached is not in the sterile field.

Prior examples of detachable sterile surgical instruments are known, but they have functional or dimensional drawbacks. In any remotely actuated system, the interface between sterile and non-sterile components must not only be designed in such a way as to maintain the sterility of, for example, the surgical instruments, but it must also provide a faithful transmission of motion from the remote actuator to the distally located instruments. Thus, each degree of freedom provided to the user of the remotely actuated system must be reproduced through transmission elements at the junction between the detachable instrument and the platform without dimensional inaccuracies or backlash. In addition, the connector element is often a single use or limited use product and so manufacturing costs should be relatively cheap. Prior interfaces, such as those shown in U.S. Pat. No. 7,699,855, have these known drawbacks due to their design elements, which typically transmit motion through reduced diameters and, thus, are susceptible to inaccuracies, backlash, other unwanted movements and incomplete transmission of motion. Prior interfaces, such as those found in U.S. Pat. No. 7,699,855 are limited-use and can only be taken through a certain number of sterilization cycles before becoming inoperative when connected with the surgical platform.

Accordingly, an aim of the present invention is to overcome the aforementioned drawbacks of known devices by providing a sterile interface for remotely actuated surgical devices wherein sterile surgical instruments can be easily attached and detached from a non-sterile surgical platform. An additional aim is for the interface to provide faithful transmission of motion from the remote, non-sterile platform to the distally located sterile surgical instruments without dimensional inaccuracies or backlash. An additional aim is to provide single use interface elements that are inexpensive to manufacture but that nevertheless have tolerances that provide for the aforementioned faithful transmission of motion. An alternative aim is to provide interface elements that are relatively inexpensive to manufacture but are designed to be taken through multiple sterilization cycles without needing to be replaced, thus reducing overall operating room costs.

SUMMARY OF THE INVENTION

These aims and other advantages are realized in a new sterile interface for the attachment of sterile surgical instruments to a non-sterile surgical platform. The sterile interface is intended to be used with articulated surgical instruments that are attached to a surgical platform. The surgical platform can be provided in the context of a mechanical telemanipulator.

In various embodiments, the sterile interface can be used in connection with a mechanical telemanipulator with a master-slave architecture and a mechanical transmission system. This enables a natural replication of user hand movements on a proximal handle at end-effector elements.

The sterile interface is designed such that surgical instruments, and in particular embodiments, laparoscopic surgical instruments, can be attached and detached from the mechanical surgical platform several times during a single surgical procedure. The sterile interface of the present invention is designed in such a way that sterilization is possible, allowing for several cycles of use before the interface elements need to be replaced.

BRIEF DESCRIPTION OF THE FIGURES

FIGS. 6 through 11 show various articulated end-effector links in various positions according to various embodiments of the present invention.

DETAILED DESCRIPTION OF THE INVENTION

Figure 1:
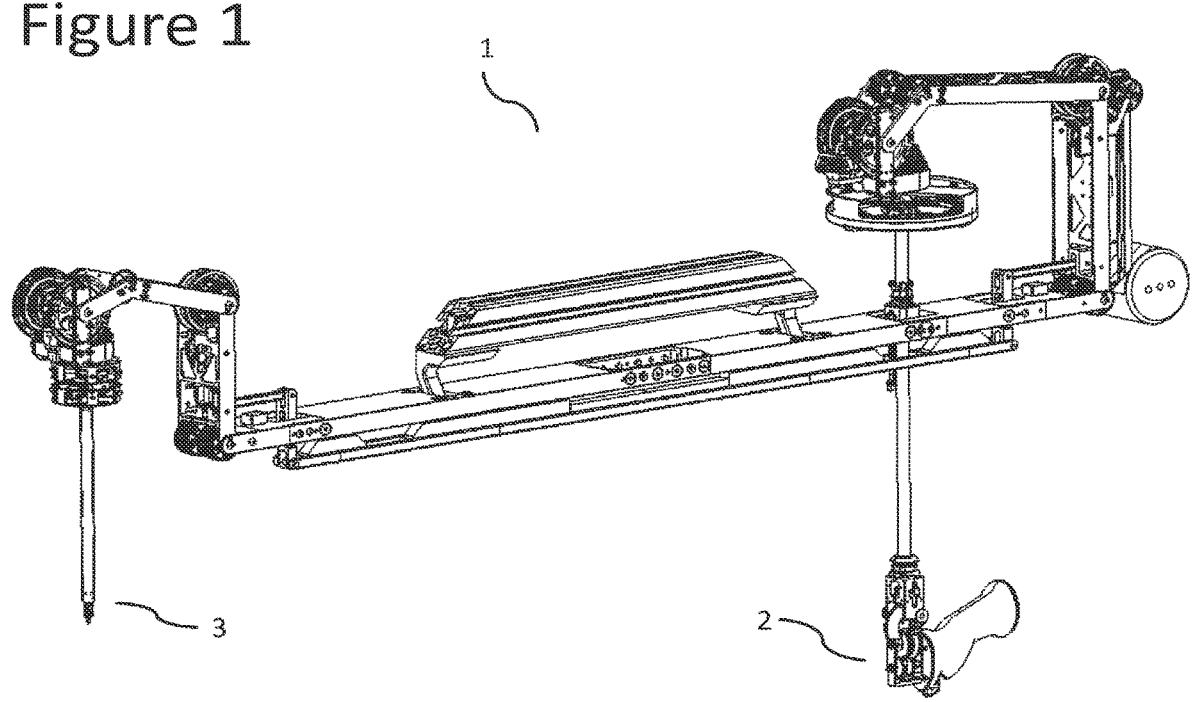
FIG. 1 shows a mechanical telemanipulator with a detachable surgical instrument according to an embodiment of the present invention.
Figure 2:
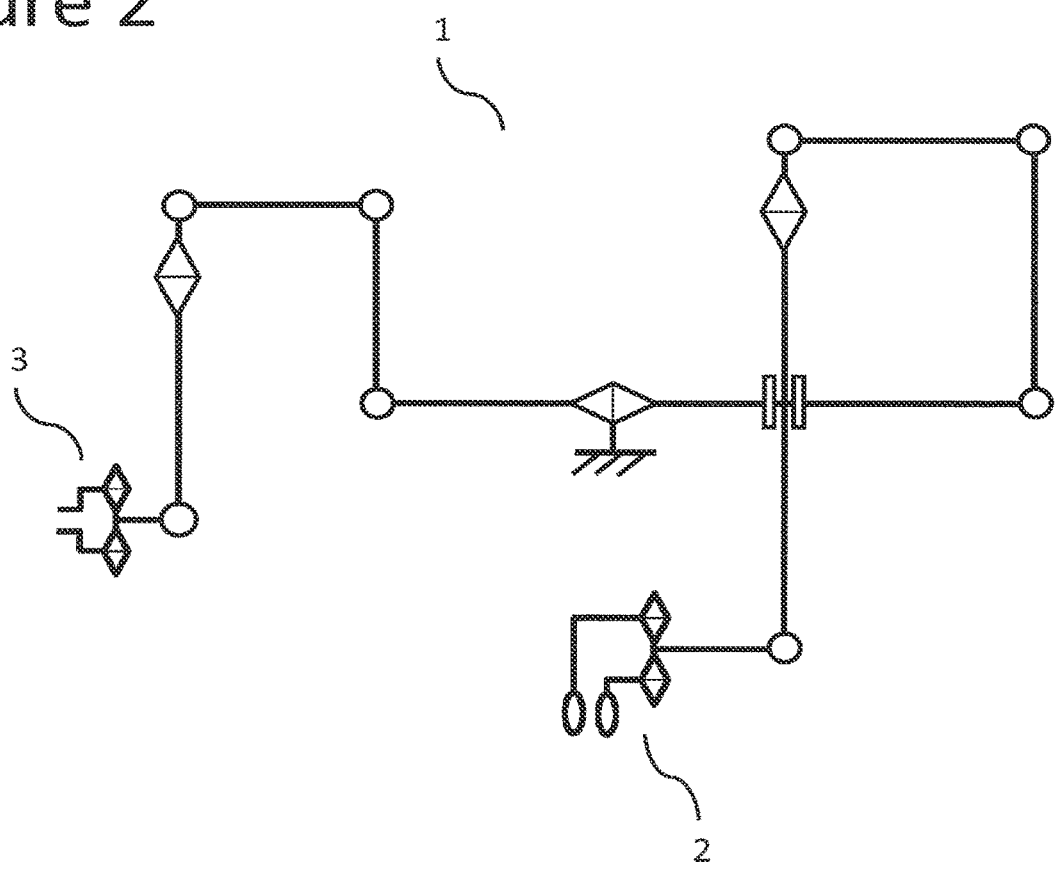
FIG. 2 shows the kinematics of a mechanical telemanipulator with a detachable surgical instrument according to an embodiment of the present invention.

The sterile interface for articulated surgical instruments, according to an embodiment of the present invention, is intended to be used in a mechanical telemanipulator 1, like the one shown in FIG. 1, whose kinematic model is shown in FIG. 2. One of the key features of this kind of mechanical telemanipulator 1 lies in a master-slave architecture and mechanical transmission system, which enable a natural replication of the user hand movements on a proximal handle 2, by the end-effector 3 of a distal surgical instrument 4 on a remote location.

Figure 3:
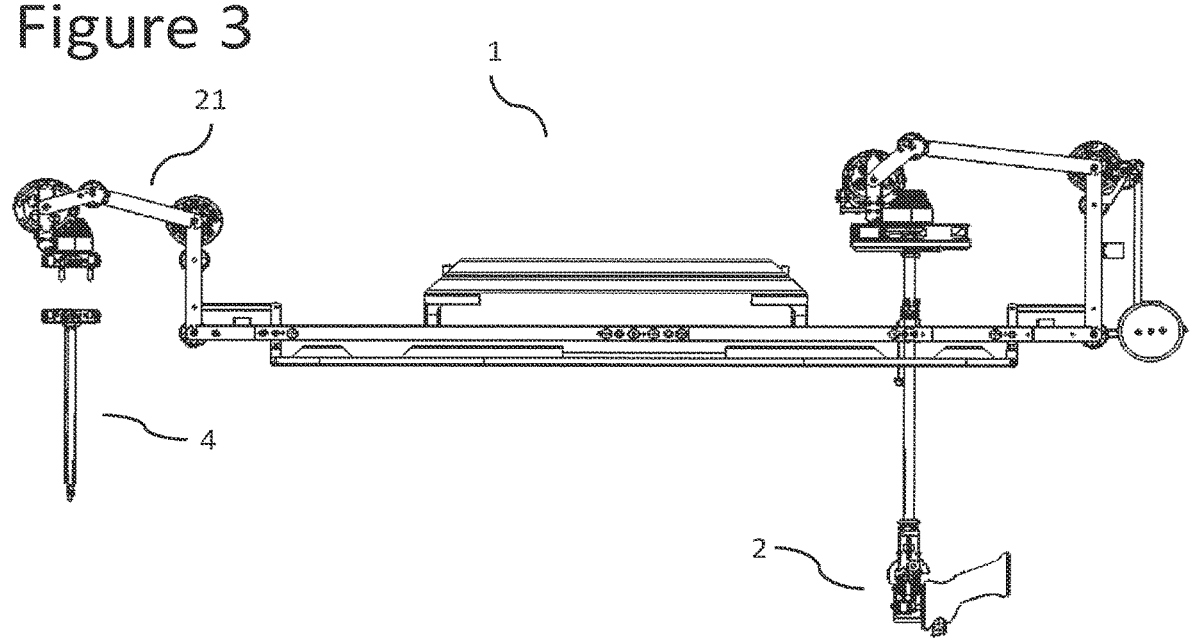
FIG. 3 shows a surgical instrument detached from a mechanical telemanipulator according to an embodiment of the present invention.
Figure 4:
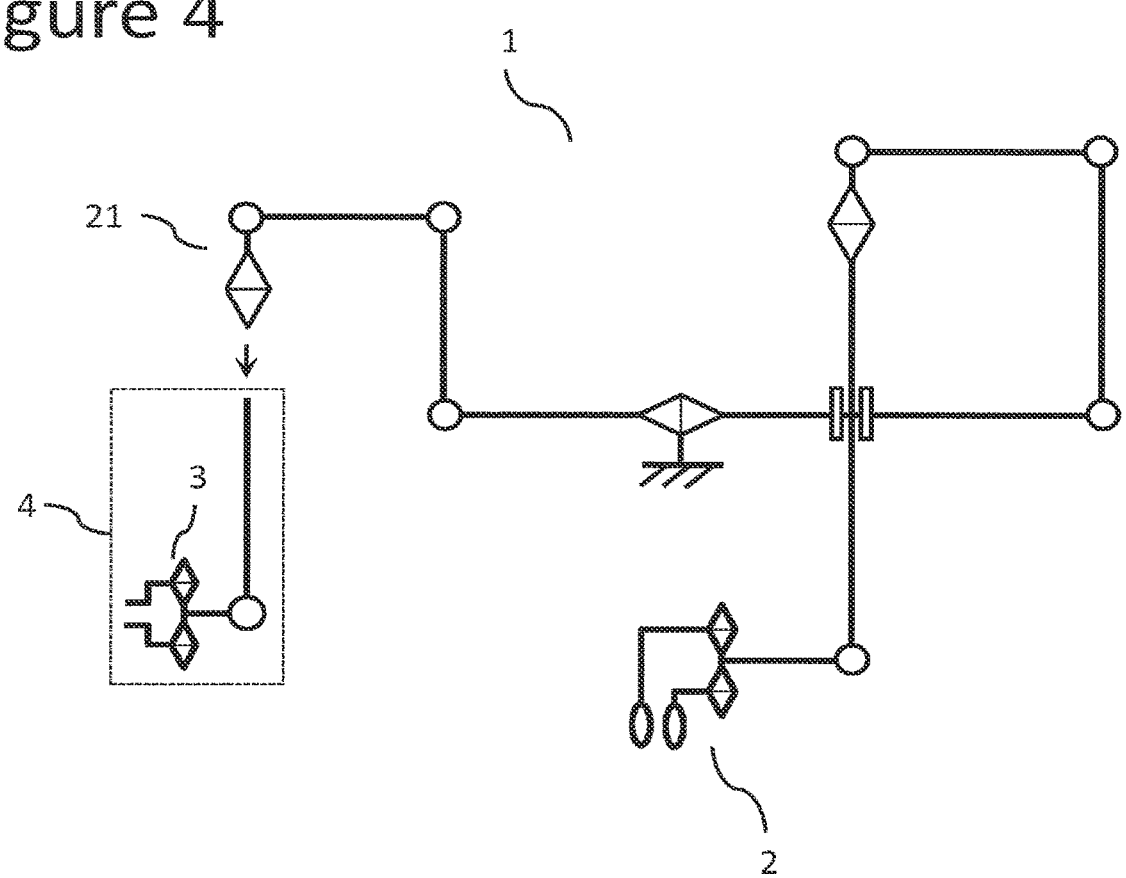
FIG. 4 shows the kinematics associated with a surgical instrument detached from a mechanical telemanipulator according to an embodiment of the present invention.

The surgical instrument 4 can take different functions and forms, like a dissector, scissor or grasper and can be plugged and unplugged from the mechanical telemanipulator 1 several times during the same surgical procedure (FIGS. 3 and 4). The remaining part of the mechanical telemanipulator 1, excluding the surgical instrument 4, is referred as the surgical platform 21. It is desirable for the surgical instruments being plugged and unplugged to be sterile while the surgical platform is non-sterile. These plugging/unplugging procedures involve not only the structural attachment/detachment of the proximal part of surgical instrument 4 to the distal part of the surgical platform 21 but also the connection/disconnection of the mechanical transmission systems that deliver motion from the different articulations of the proximal handle 2 to the equivalent articulations of the end-effector 3. In addition, these plugging/unplugging procedures have to be easily and quickly performed by the surgeons during the surgical procedure in order to avoid long and frustrating breaks in the surgeon's workflow.

Figure 5:
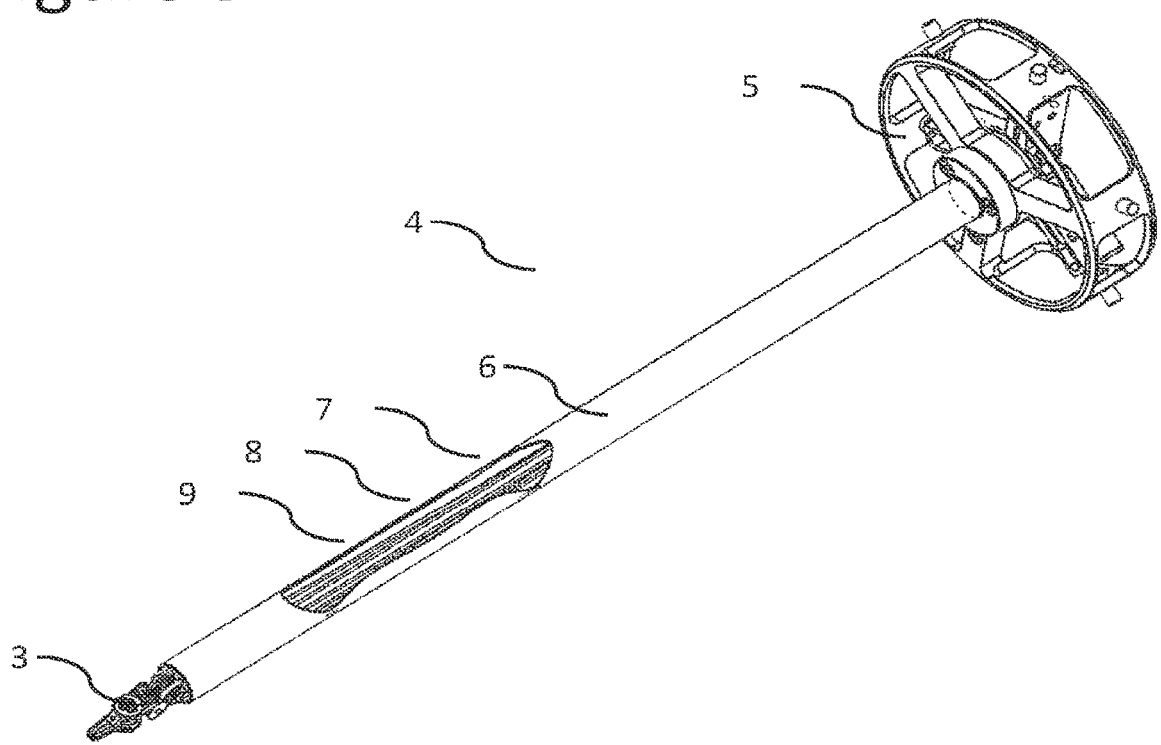
FIG. 5 shows a detachable surgical instrument according to an embodiment of the present invention.
Figure 6:
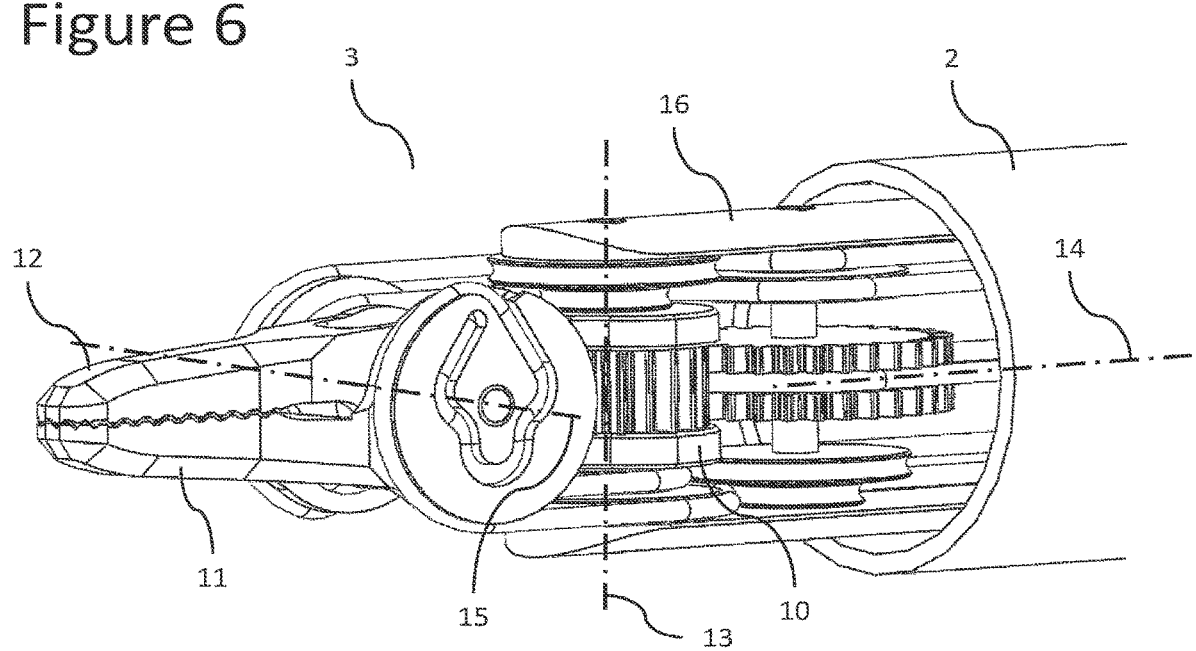
Figure 10:
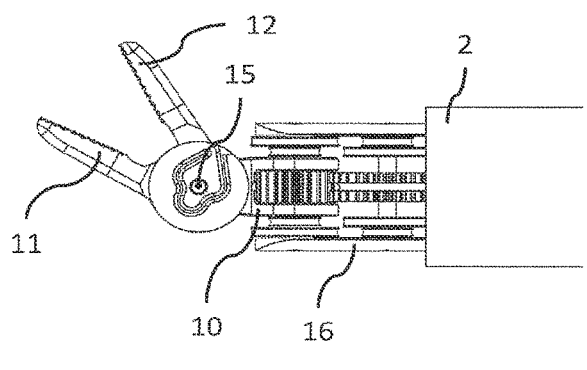
Figure 11:
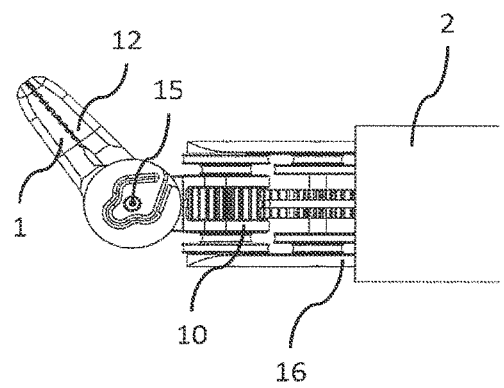

A surgical instrument 4 for minimally invasive surgical procedures, being able to be connected to an embodiment of the sterile surgical interface of the present invention, is described herein, and is seen generally in FIG. 5. This surgical instrument 4 includes a distal articulated end-effector 3, a proximal hub 5 and a main shaft 6, through which different mechanical elements 7, 8, 9 may pass, delivering motion to the different end-effector links 10, 11, 12 (FIG. 6) from the proximal hub 5. Referring to FIG. 6, the end-effector 3 is connected to the distal extremity of the main shaft 6 by a proximal joint, which allows the rotation of the proximal end-effector link 10 by the proximal axis 13 in such a manner that the orientation of the proximal end-effector link 10 with respect to the main shaft axis 14 can be changed. The distal end-effector links 11, 12 are pivotally connected to the proximal end-effector link 10 by two distal joints, having coincident axes of rotation, which are represented by the distal axis 15. This distal axis 15 is substantially perpendicular and non-intersecting with the proximal axis 13 and substantially intersects the main shaft axis 14. FIGS. 7 to 11 show the surgical instrument 4 with different angular displacements at the end-effector joints.

Figure 12:
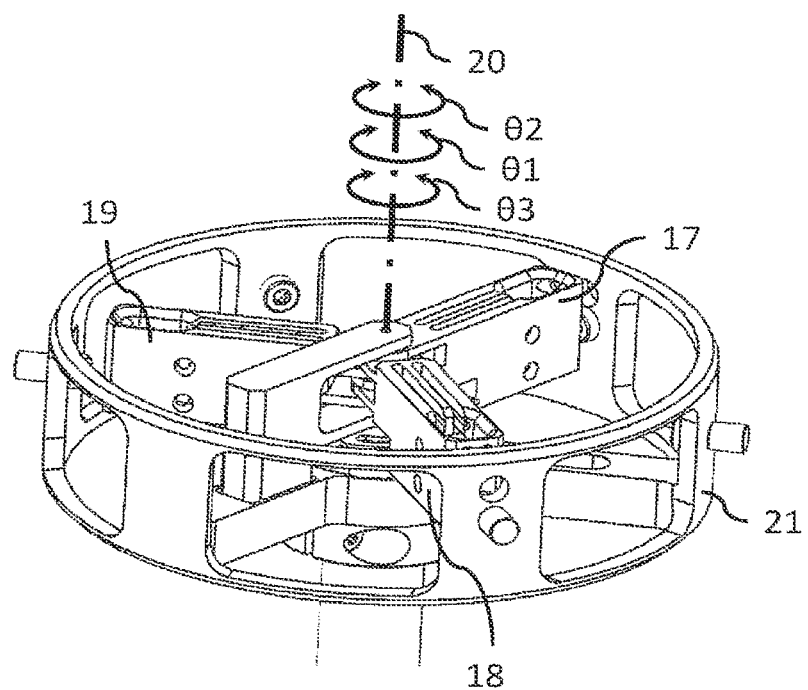
FIG. 12 shows the rotational elements of an interface portion of a surgical instrument according to an embodiment of the present invention.
Figure 13:
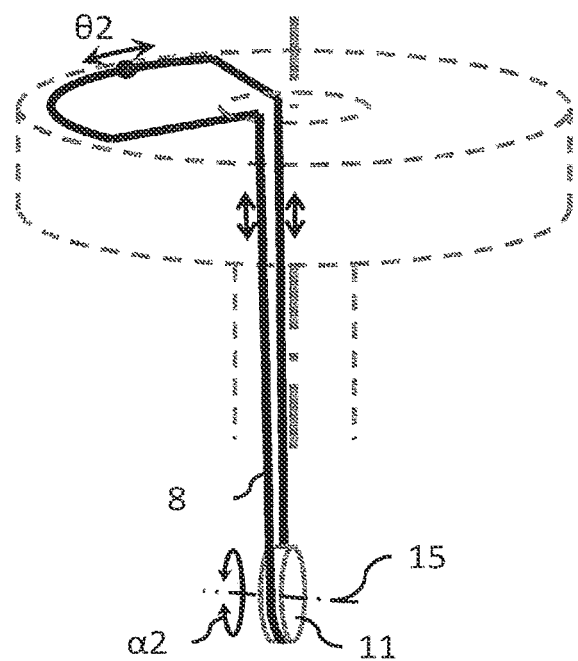
FIG. 13 shows the rotational kinematics of an interface portion of a surgical instrument according to an embodiment of the present invention.
Figure 14:
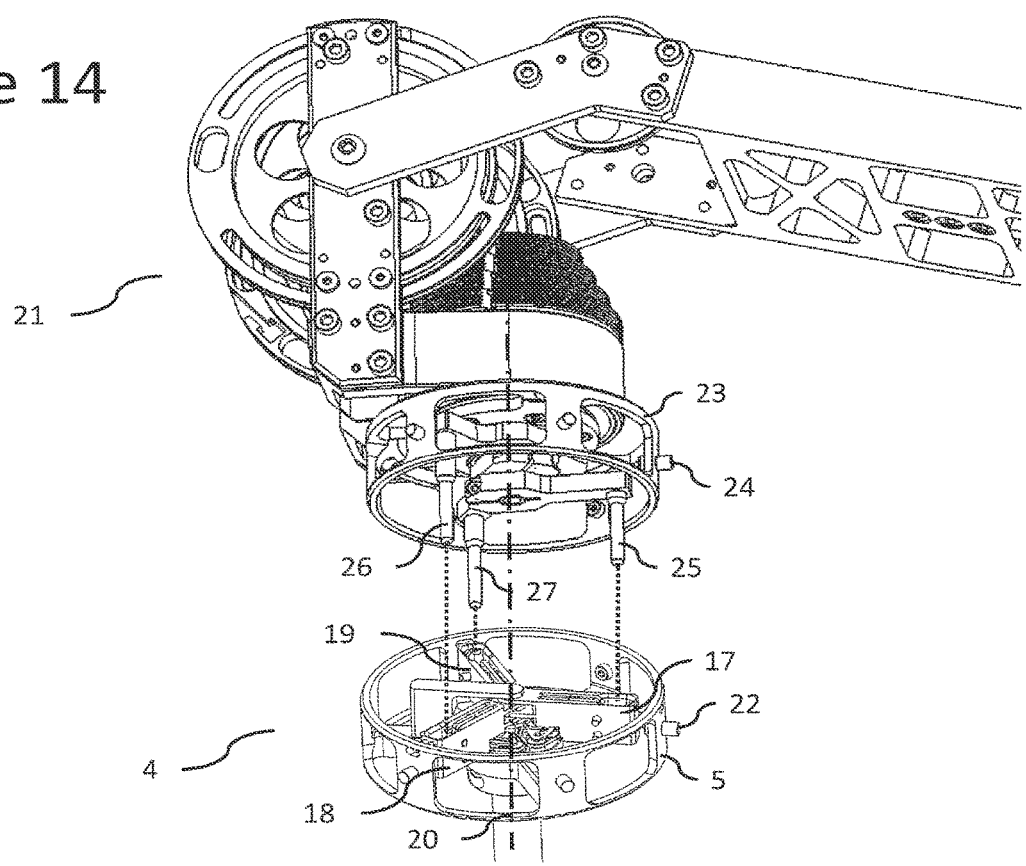
FIG. 14 shows a schematic view of the rotational elements of an interface portion of a surgical instrument according to an embodiment of the present invention.

With reference to FIGS. 12 and 13, the movement is transmitted to each one of the three distal articulations of the instrument 4 by a rotating element 17, 18, 19, which is able to rotate about an axis 20 and is connected to a transmission element 7, 8, 9. As a result, when the rotating element 17, 18, 19 rotates a certain angle θ1, θ2, θ3 about the axis 20, a rotation α1, α2, α3 is transmitted to the respective end-effector link 10, 11, 12. Accordingly, FIG. 14 shows how the movement is transmitted to the rotating elements 17, 18, 19 of the surgical instrument 4 from the distal part of the surgical platform 21. The cylindrical elements 25, 26, 27, which are mounted inside the housing element 23, are able to translate along circular paths that are collinear with the axis 20. When the proximal hub 5 is attached to the housing element 23, the cylindrical elements 25, 26, 27 can be respectively connected to the rotating elements 17, 18, 19, so that the movements generated at the handle 2 can be transmitted to the three end-effector links 10, 11, 12 by the transmission elements 7, 8, 9.

Figure 15:
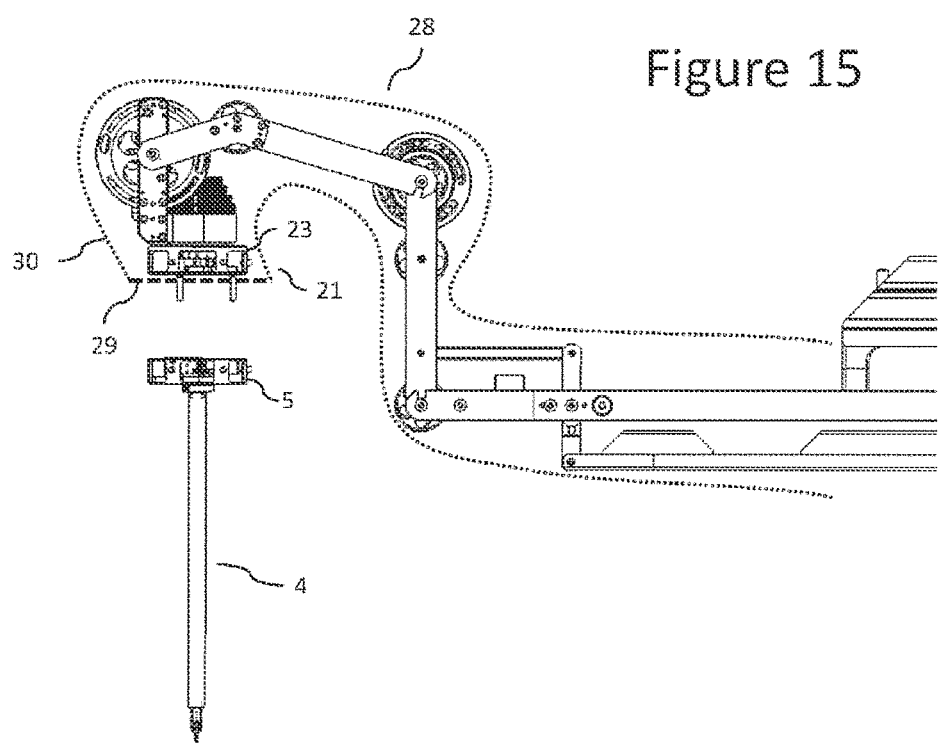
FIGS. 15 and 16 show the mechanical transmission elements of a mechanical telemanipulator in conjunction with a detached surgical instrument according to an embodiment of the present invention.

Since the surgical instrument 4 is entering the patient's body, it has to be sterile, just like the area in the vicinity of the patient. On the other hand, the surgical platform 21 is not sterile (and it is not desirable to have the entire surgical platform be part of the sterile field as this would not be practical in view of normal operating room workflow) and therefore should be separated from the sterile instrument portions by the sterile interface 28, which protects the sterile area from the non-sterile components of the surgical platform 21 (FIG. 15).

The sterile interface 28 comprises two main components: a flexible sleeve 30, which covers the moving links of the surgical platform 21 and a rigid connector 29, which i) guarantees that the sterile instrument 4 is not directly touching non-sterile components, ii) enables attachment/detachment between the surgical instrument 4 and the surgical platform 21, and iii) ensures the connection/disconnection of the mechanical transmission systems that deliver motion to the end-effector links 10, 11, 12. Full connection of the mechanical transmission systems during operation of the platform is necessary for faithful replication of operator hand movements at the end effector.

Figure 16:
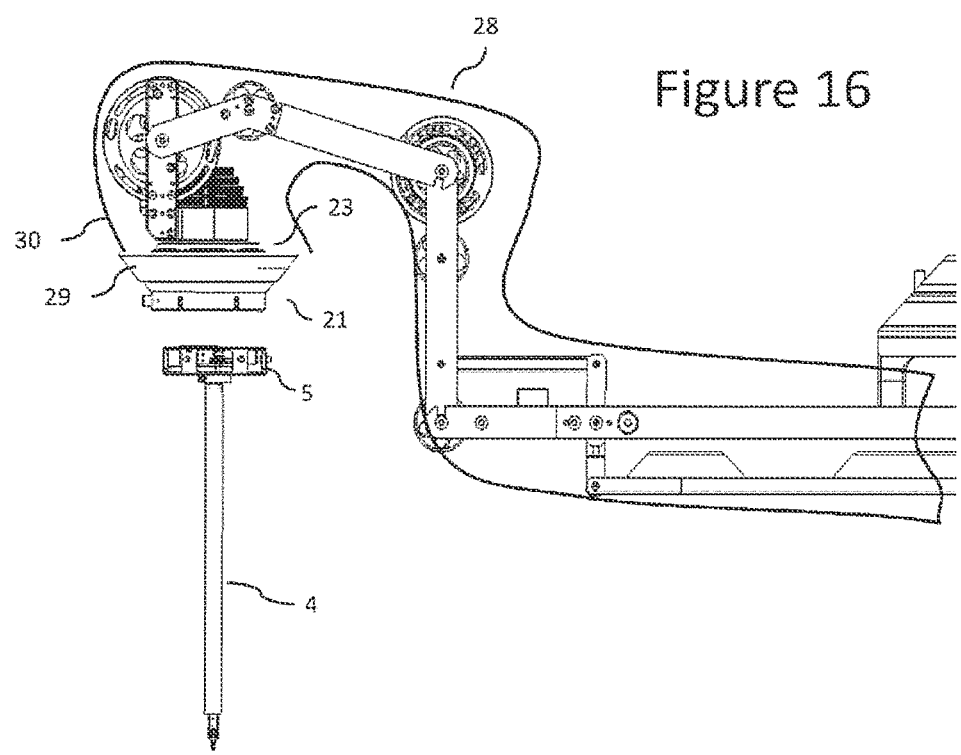
Figure 17:
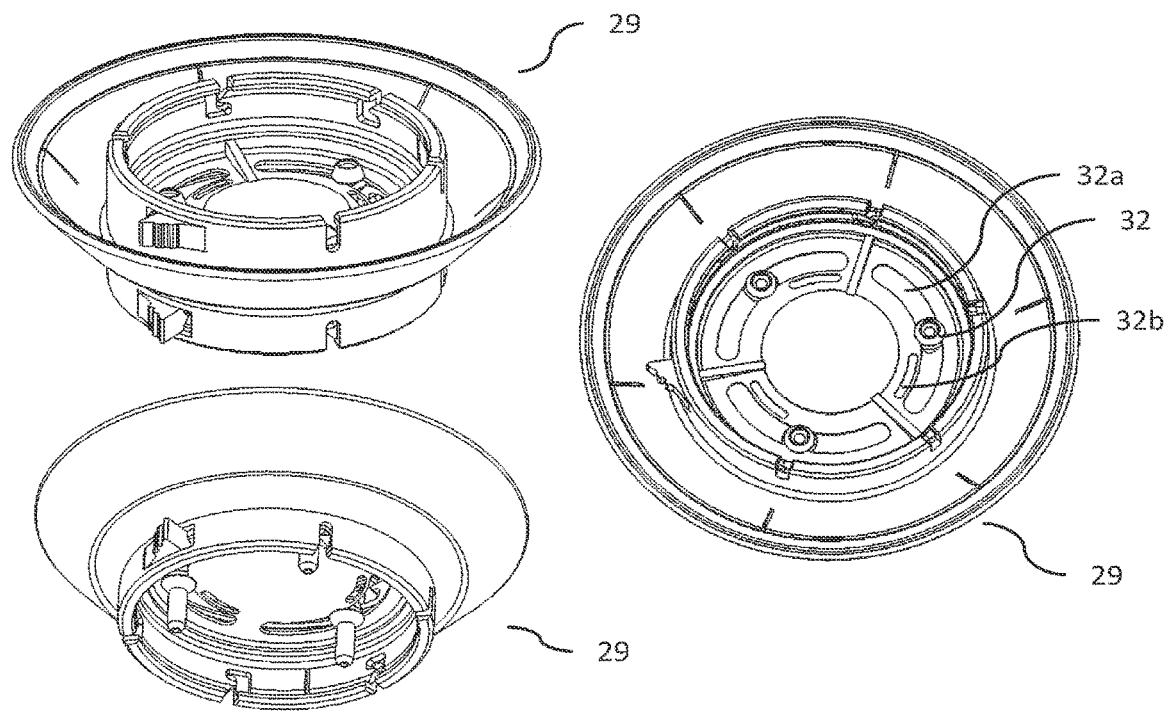
FIG. 17 through 21 show various perspective views of an interface element in accordance with various embodiments of the present invention.
Figure 18:
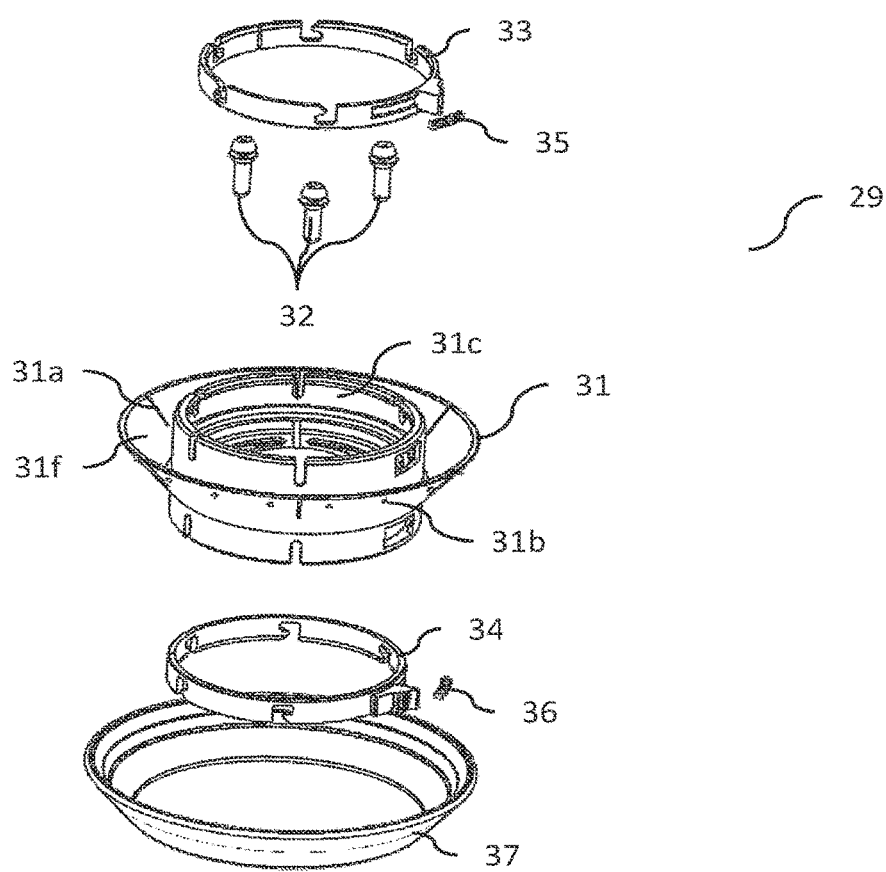

FIG. 16 shows an embodiment of the current invention where the sterile interface 28 comprises a plastic flexible sleeve 30 and a multi-component plastic rigid connector 29. This plastic rigid connector 29 can be either sterilisable/reprocessable or single-use. However, in this particular embodiment, it is considered to be single-use, just like the plastic flexible sleeve 30. FIGS. 17 and 18 show different 3D views of the rigid connector 29, with its multiple components 31, 32, 33, 34, 35, 36, 37. The three miniature cups 32 are able to move along three circular grooves 32a, where they are inserted at the level of the insertion grooves 32b. The core component 31 has two surfaces 31c where the rings 33 and 34 can rotate, actuated by the compression springs 35 and 36. The fixation ring 37 can be attached to the core component 31 by the deformation of the flanged surface 31f where the grooves 31a and the sharp points 31b are located.

Figure 19:
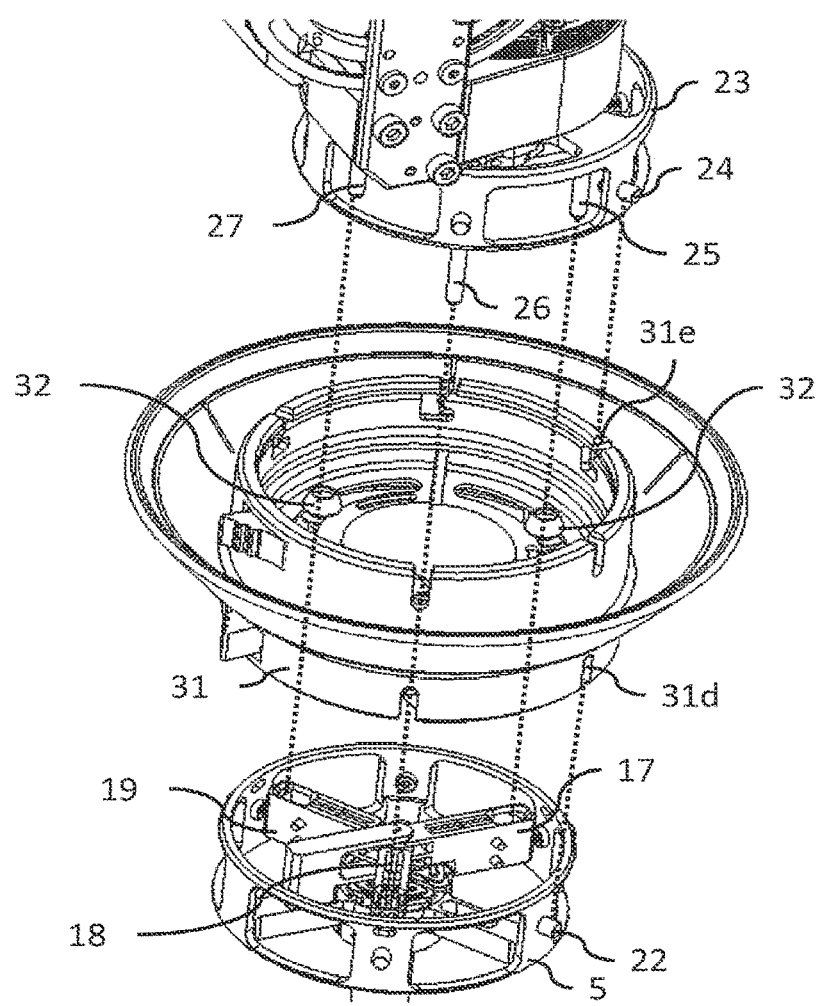

FIG. 19 shows how the rigid connector 29 can be positioned and operationally connected between the proximal hub 5 of the surgical instrument 4 and the housing element 23 of the surgical platform 21. In order to connect/disconnect the mechanical transmission systems that deliver motion to the end-effector links 10, 11, 12 the cylindrical elements 25, 26, 27 are inserted on the three miniature cups 32, which are then inserted on the rotating elements 17, 18, 19. In this way, it can be guaranteed that the sterile surgical instrument 4 is not directly touching non-sterile components. Since the rigid connector 29 can be a single-use product, its manufacturing processes have to guarantee fairly low production costs, which typically cannot deliver very accurate components. Therefore, by transmitting the movement, through the miniature cups 32, with translations on a maximized-diameter-circular path, this interface is less sensitive to dimensional inaccuracies or backlash between matching components. This is an improvement over other known devices where movement is transmitted by rotations with reduced diameters. A further advantage of this interface 28 pertains to its axisymmetric geometry, which is volumetrically optimized for rotations about the main shaft axis 14.

Figure 24:
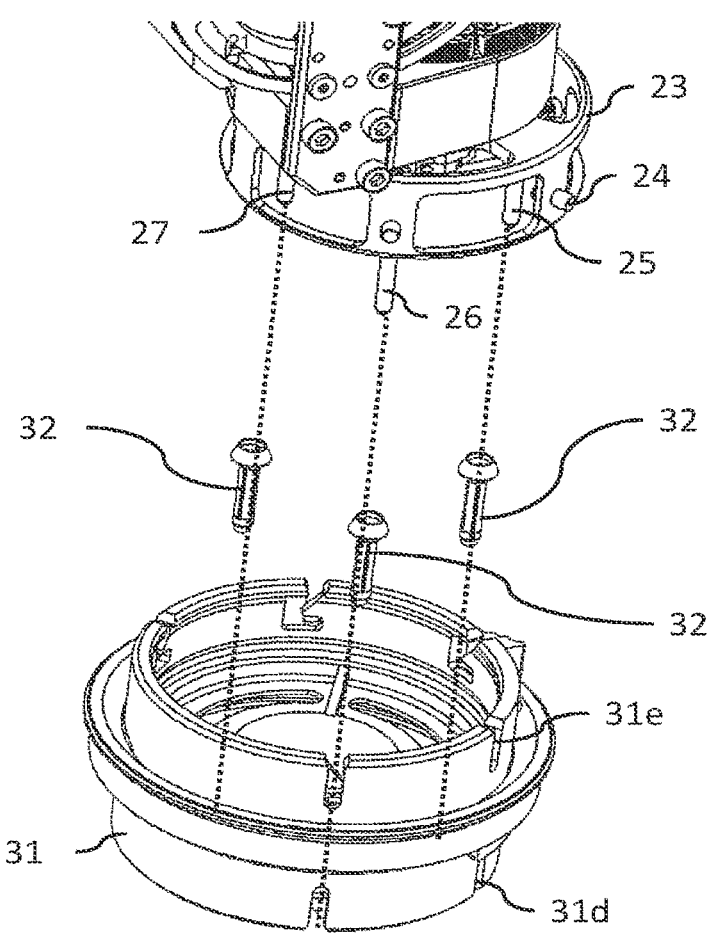
FIGS. 24 and 25 show perspective views of the attachment of elements of a surgical instrument to a surgical platform according to an embodiment of the present invention.
Figure 25:
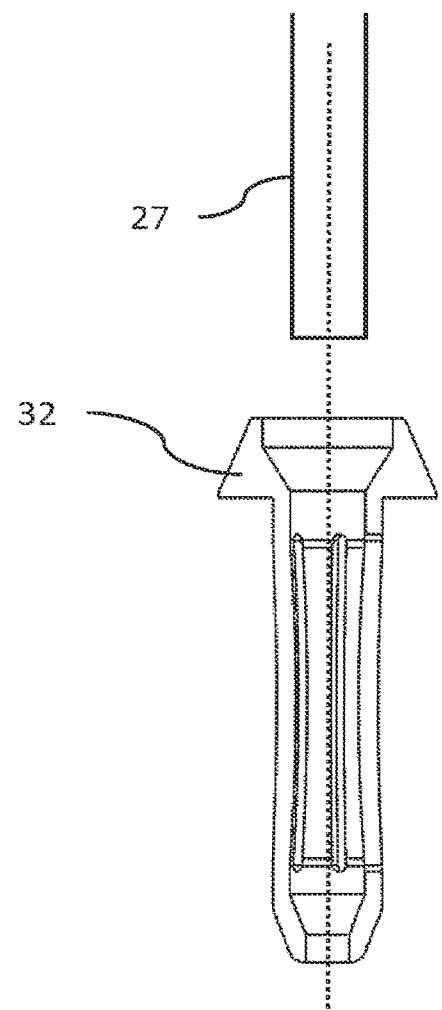

In another embodiment of the current invention (FIG. 24), the miniature cups 32 don't need to be pre-inserted in the three circular grooves 32a. Instead, they have a geometry which enables them to be pre-inserted directly on the cylindrical elements 25, 26, 27 before the attachment of the core element 31 on the housing element 23. As shown in FIG. 25, the miniature cups 32 can be attached directly to the cylindrical elements 25, 26, 27 thanks to their geometry, which comprises multiple longitudinal groves that enable the miniature cups to expand radially when the cylindrical elements 25, 26, 27 are inserted. Other solutions for the attachment of the miniature cups 32 on the cylindrical elements 25, 26, 27 can be used, using deformable components (like the one shown in FIG. 25) or non-deformable components (for instance, using threaded surfaces, the miniature cups 32 can be screwed on the cylindrical elements 25, 26, 27, or using magnets).

The structural attachment/detachment between the surgical instrument 4 and the remaining part of the surgical platform 21 is made by inserting the five radially-displaced platform pins 24 in the five radially-displaced connector grooves 31e. On the surgical instrument 4 side, the five radially-displaced instrument pins 22 are inserted in the five radially-displaced connector grooves 31d. As can be seen in FIG. 19, these two attachment mechanisms, used to attach the rigid connector 29 on the surgical platform 21 and the surgical instrument 4 on the rigid connector 29, have axi-asymmetric features or geometries (in the current embodiment, axi-asymmetric placement of radially-displaced pins and connector grooves) that prevent users from inserting the sterile articulated instruments on a wrong axial direction.

Figure 20:
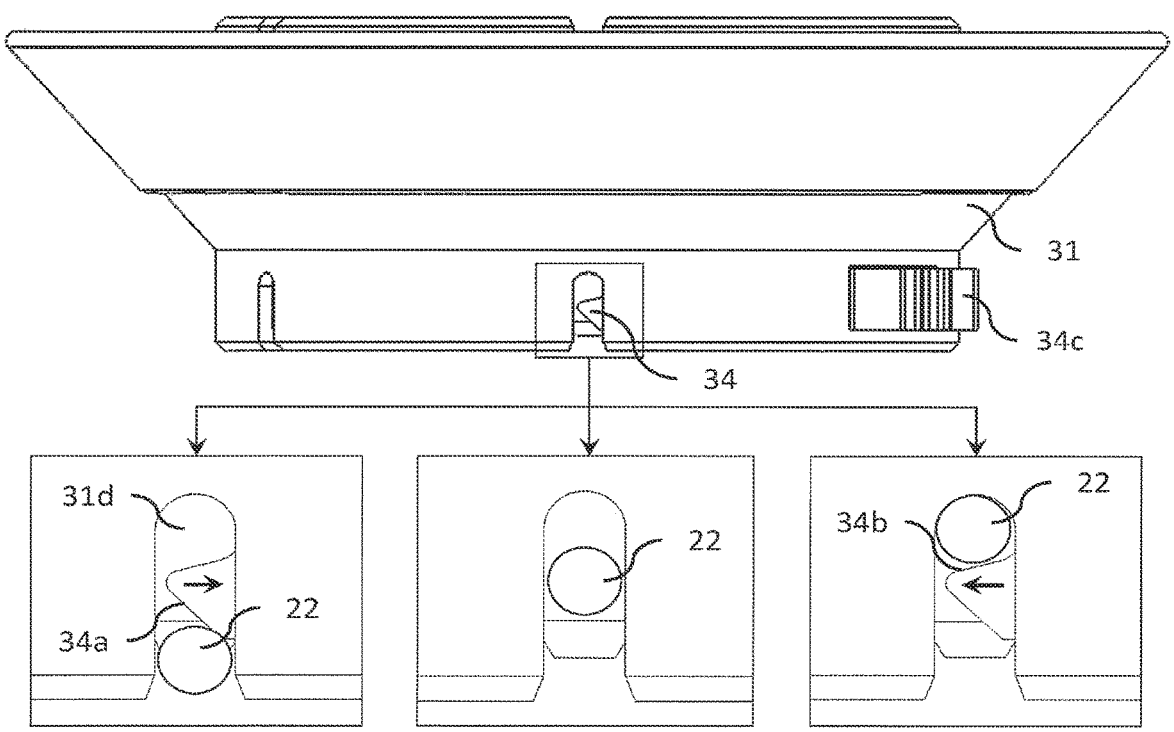

FIG. 20 shows in detail the attachment mechanism between each instrument pin 22 and the respective connector groove 31d. When the instrument pin 22 enters the connector groove 31d, it touches the angular surface 34a of the ring 34, causing its angular displacement against the compression spring 36. This angular displacement allows the instrument pin 22 to reach the end of the connector groove 31d, where it is kept in place by the action of the compression spring 36, whose force presses the angular surface 34b of the ring 34 against the instrument pin 22. This sequence is simultaneously done at all the radially-displaced instrument pins 22, guaranteeing the structural attachment between the surgical instrument 4 and the rigid connector 29. The structural detachment between the surgical instrument 4 and the rigid connector 29 is achieved by the reverse sequence of actions. The structural attachment/detachment between the rigid connector 29 and the housing element 23 of the surgical platform 21 is performed in a similar interaction between each platform pin 24 and its respective connector groove 31e.

Figure 21:
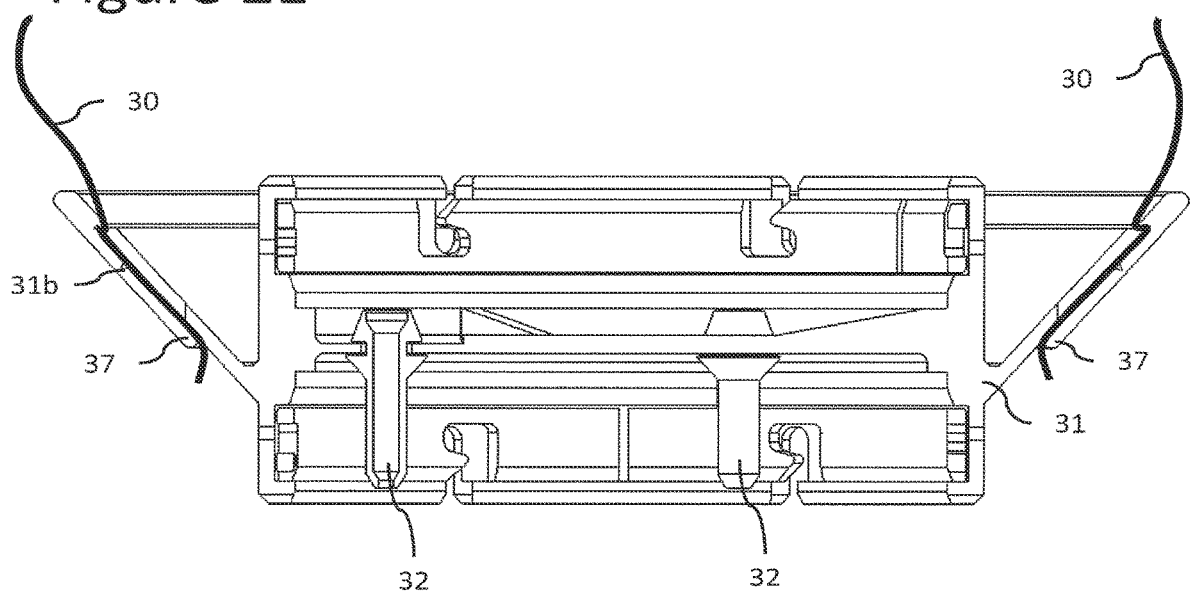

FIG. 21 shows how the flexible sleeve 30 can be releasably attached to the rigid connector 29, by being squeezed between the flanged surface 31f of the core component 31 and the fixation ring 37. The indentation of the sharp points 31b on the flexible sleeve 30 reinforces the attachment. This method of attachment is an improvement over prior art interfaces where the flexible sleeve 30 is glued or welded to the rigid connector 29, which jeopardizes the possibility of having the flexible sleeve 30 as a single-use product and the rigid connector 29 as a reusable device. Therefore, with this feature in the interface as per the current invention, the rigid connector 29 can be cleaned and sterilized after each procedure, which can significantly reduce procedure costs over the use of prior art solutions.

Figure 26:
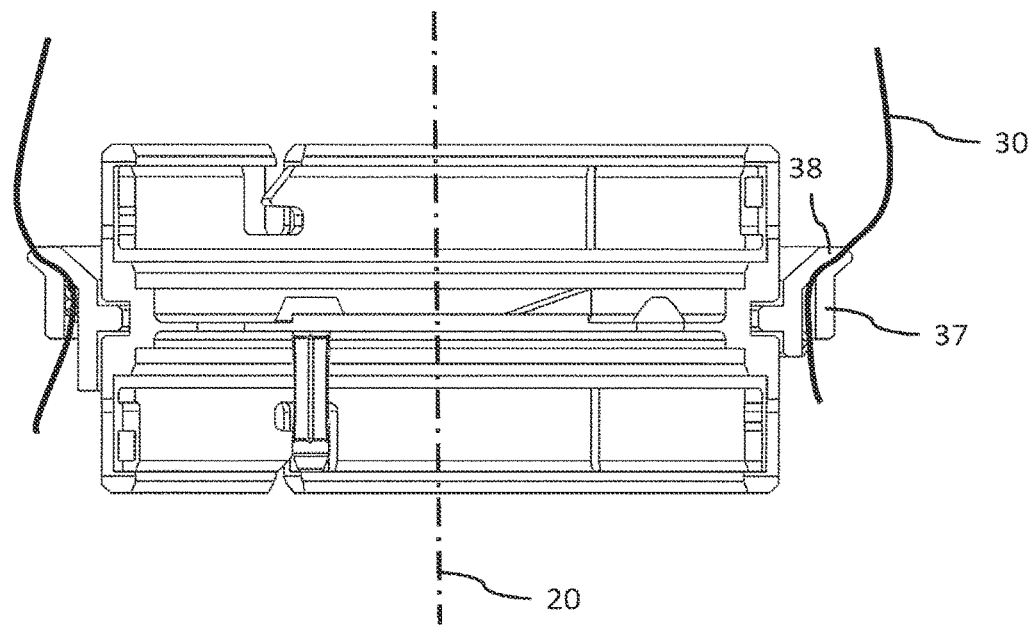
FIG. 26 shows a perspective view of various elements of a fixation ring for attachment of a sterile cover according to an embodiment of the present invention.

In another embodiment of the current invention (FIG. 26), the fixation ring 37 may be fixed to a rotating ring 38, which is able to freely rotate around the core component 31. In this embodiment, the flexible sleeve 30 is squeezed between the fixation ring 37 and the rotating ring 38 and its torsional deformation is minimized when the core component 31 is rotated around the axis 20 by the platform 21.

Figure 22:
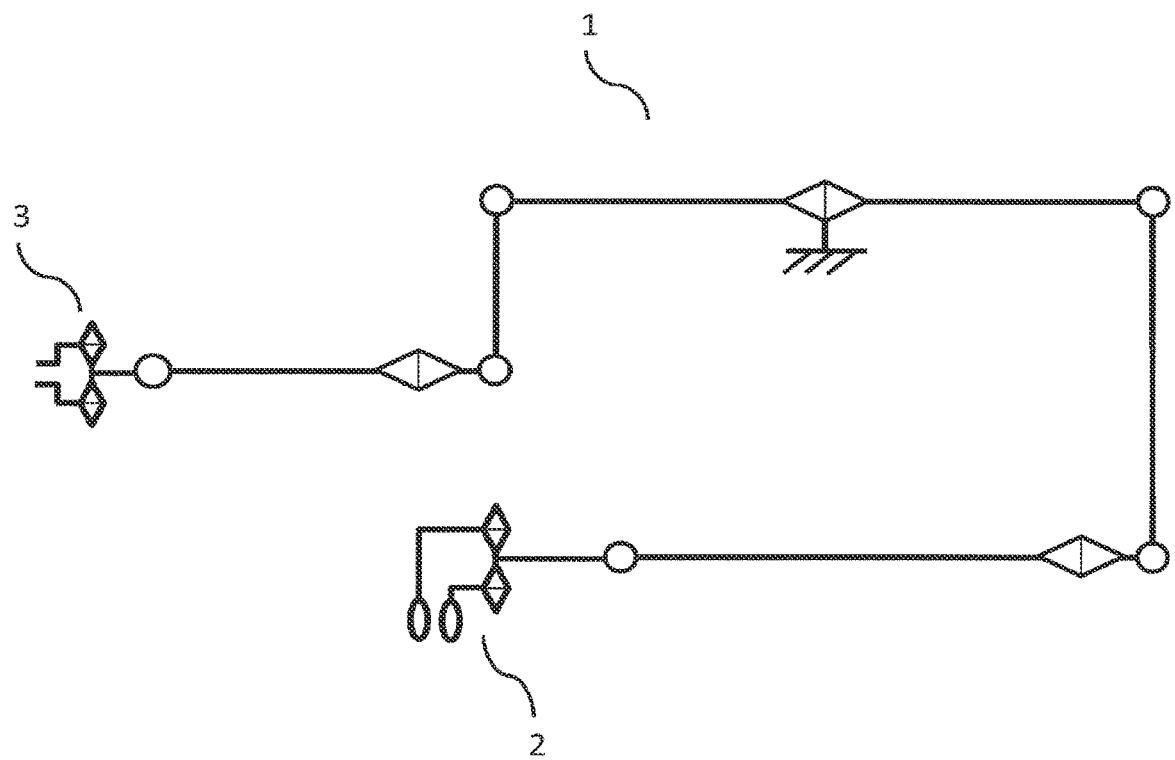
FIGS. 22 and 23 show schematic views of kinematics associated with a mechanical telemanipulator according to an embodiment of the present invention.
Figure 23:
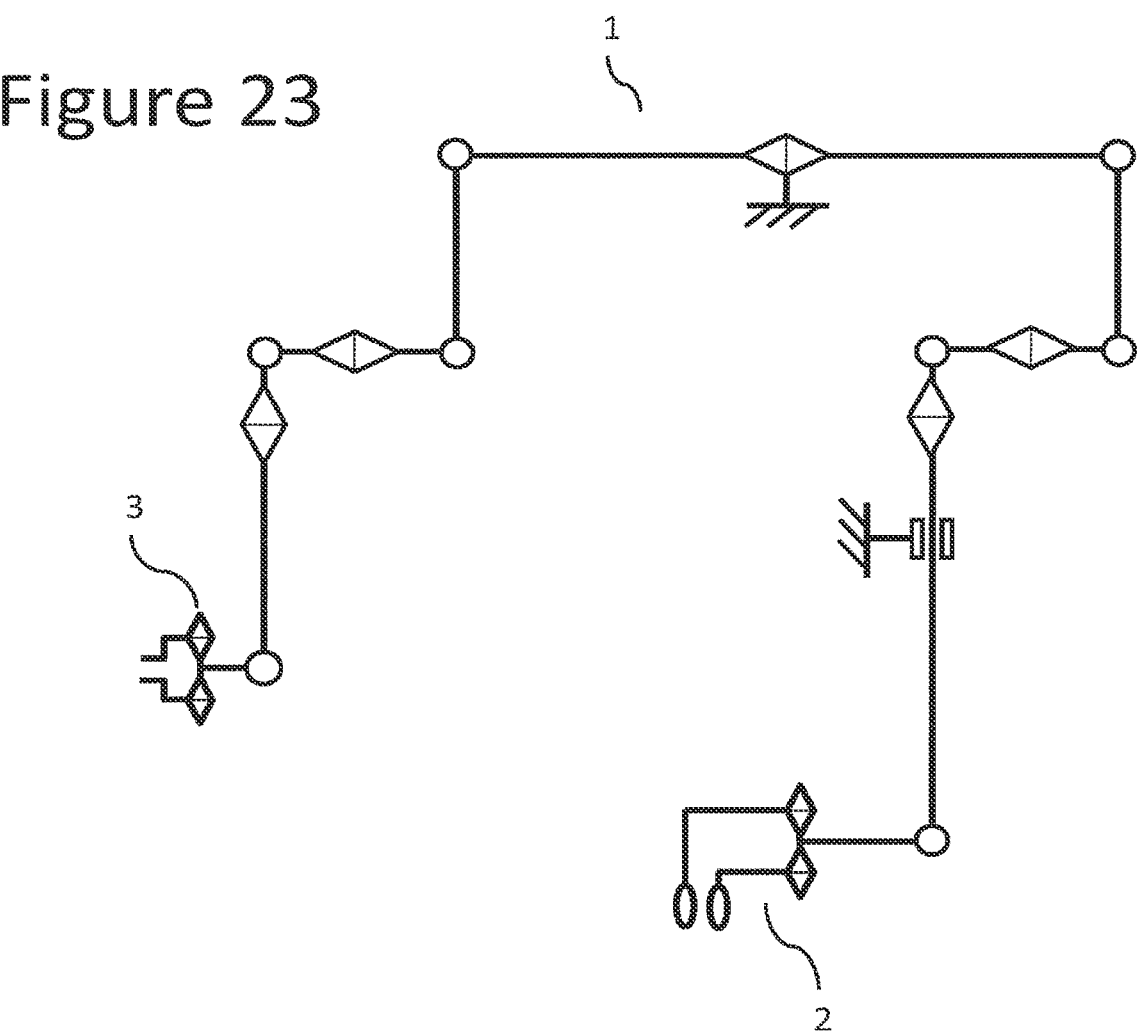

While this invention has been shown and described with reference to particular embodiments thereof, it will be understood by those skilled in the art that various changes in form and details may be made therein without departing from the spirit and scope of the invention as defined by the appended claims. For instance, the mechanical telemanipulator 1 can assume other kinematics, like the ones shown in FIGS. 22 and 23. In addition, while the sterile interface of the present invention has been primarily described in connection with a laparoscopic surgical platform, one of skill in the art will understand that the sterile interface could easily be used with other surgical platforms, such as open field systems. In addition, the current sterile interface could be used with other telemanipulator or remote actuation systems in other sterile situations outside of the surgical context.

The invention claimed is:

1. A method for maintaining sterility of surgical instruments during a surgical procedure, the method comprising:
   locking a rigid connector to a surgical platform;
   locking the rigid connector to a proximal hub of an articulated surgical instrument;
   covering moving links of the surgical platform with a flexible sleeve coupled to the rigid connector;
   moving an end-effector of the articulated surgical instrument responsive to movement at the surgical platform to perform the surgical procedure while maintaining sterility of the articulated surgical instrument during the surgical procedure;
   detaching the articulated surgical instrument from the rigid connector; and
   removing the flexible sleeve from the surgical platform.

2. The method of claim 1, wherein covering moving links of the surgical platform via the flexible sleeve ensures that the articulated surgical instrument is not directly touching the surgical platform during the surgical procedure.

3. The method of claim 1, further comprising mating at least one miniature cup with both a mechanical transmission from the surgical platform and a mechanical transmission of the articulated surgical instrument.

4. The method of claim 1, wherein removing the flexible sleeve from the surgical platform comprises detaching the flexible sleeve from the rigid connector.

5. The method of claim 1, further comprising attaching and detaching the articulated surgical instrument from the surgical platform several times during the surgical procedure.

6. The method of claim 1, further comprising sterilizing the rigid connector after each surgical procedure.

7. The method of claim 1, wherein locking the rigid connector to the surgical platform comprises locking a first ring of the rigid connector with a second ring of the rigid connector.

8. The method of claim 7, wherein moving the end-effector of the articulated surgical instrument responsive to movement at the surgical platform comprises moving the end-effector of the articulated surgical instrument responsive to movement at the surgical platform via a core of the rigid connector, the core concentric with and extending between the first ring and the second ring.

9. The method of claim 1, wherein locking the rigid connector to the proximal hub of the articulated surgical instrument comprising locking the rigid connector to the proximal hub of the articulated surgical instrument such that the articulated surgical instrument does not contact non-sterile components of the surgical platform.

10. The method of claim 1, wherein the rigid connector comprises axi-asymmetric features or geometries that prevent users from inserting the articulated surgical instrument in an incorrect axial position.

11. The method of claim 1, further comprising connecting a mechanical transmission to deliver motion from the surgical platform to the articulated surgical instrument.

12. The method of claim 11, wherein moving the end-effector of the articulated surgical instrument responsive to movement at the surgical platform comprises delivering motion from the surgical platform to the articulated surgical instrument via the mechanical transmission.

13. The method of claim 1, further comprising engaging a rotating ring with a fixation ring to capture a portion of the flexible sleeve therebetween to couple the flexible sleeve to the rigid connector, the rotating ring configured to freely rotate around the rigid connector.

14. A method for maintaining sterility of surgical instruments during a surgical procedure, the method comprising:
   locking a rigid connector to a surgical platform;
   attaching a proximal hub of an articulated surgical instrument to the rigid connector without contacting non-sterile components of the surgical platform;
   covering moving links of the surgical platform with a flexible sleeve coupled to the rigid connector; and
   moving an end-effector of the articulated surgical instrument responsive to movement at the surgical platform to perform the surgical procedure while maintaining sterility of the articulated surgical instrument during the surgical procedure.

15. The method of claim 14, wherein locking the rigid connector to the surgical platform comprises locking a first ring of the rigid connector with a second ring of the rigid connector.

16. The method of claim 15, wherein moving the end-effector of the articulated surgical instrument responsive to movement at the surgical platform comprises moving the end-effector of the articulated surgical instrument responsive to movement at the surgical platform via a core of the rigid connector, the core concentric with and extending between the first ring and the second ring.

17. The method of claim 14, wherein the rigid connector comprises axi-asymmetric features or geometries that prevent users from inserting the articulated surgical instrument in an incorrect axial position.

18. The method of claim 14, further comprising connecting a mechanical transmission to deliver motion from the surgical platform to the articulated surgical instrument.

19. The method of claim 18, wherein moving the end-effector of the articulated surgical instrument responsive to movement at the surgical platform comprises delivering motion from the surgical platform to the articulated surgical instrument via the mechanical transmission.

20. The method of claim 14, further comprising engaging a rotating ring with a fixation ring to capture a portion of the flexible sleeve therebetween to couple the flexible sleeve to the rigid connector, the rotating ring configured to freely rotate around the rigid connector.

* * * * *